(12) United States Patent
Vanslyke et al.

(10) Patent No.: US 12,697,049 B2
(45) Date of Patent: Aug. 4, 2026

(54) CONTINUOUS GLUCOSE MONITORS AND RELATED SENSORS UTILIZING MIXED MODEL AND BAYESIAN CALIBRATION ALGORITHMS

(71) Applicant: DexCom, Inc., San Diego, CA (US)

(72) Inventors: Stephen J. Vanslyke, Carlsbad, CA (US); Giada Acciaroli, Ceggia (IT); Martina Vettoretti, Valla' di Riese Pio X (IT); Andrea Facchinetti, Trissino (IT); Giovanni Sparacino, Padua (IT)

(73) Assignee: Dexcom, Inc., San Diego, CA (US)

( * ) Notice: Subject to any disclaimer, the term of this patent is extended or adjusted under 35 U.S.C. 154(b) by 1162 days.

(21) Appl. No.: 16/779,503

(22) Filed: Jan. 31, 2020

(65) Prior Publication Data

US 2020/0237271 A1    Jul. 30, 2020

Related U.S. Application Data

(63) Continuation of application No. PCT/IB2018/056295, filed on Aug. 20, 2018.

(Continued)

(51) Int. Cl.
*A61B 5/145* (2006.01)
*A61B 5/00* (2006.01)

(52) U.S. Cl.
CPC ........ *A61B 5/14532* (2013.01); *A61B 5/1451* (2013.01); *A61B 5/14546* (2013.01);
(Continued)

(58) Field of Classification Search
CPC . A61B 5/1451; A61B 5/14532; A61B 5/1459; A61B 5/1486–14865;
(Continued)

(56) References Cited

U.S. PATENT DOCUMENTS 6,424,847 B1    7/2002  Mastrototaro et al.
6,477,395 B2    11/2002  Schulman et al.
(Continued)

FOREIGN PATENT DOCUMENTS

EP          3672479 A1    7/2020
WO    WO-2017035022 A1 *  3/2017    ......... A61B 5/14532

OTHER PUBLICATIONS

G. Acciaroli, M. Vettoretti, A. Facchinetti, G. Sparacino and C. Cobelli, "Reduction of Blood Glucose Measurements to Calibrate Subcutaneous Glucose Sensors: A Bayesian Multiday Framework," May 23, 2017, IEEE, doi: 10.1109/TBME.2017.2706974 (Year: 2017).*

(Continued)

*Primary Examiner* — Eric J Messersmith
(74) *Attorney, Agent, or Firm* — Schwegman, Lundberg & Woessner, P.A.

(57)          ABSTRACT

A method for monitoring a blood glucose level of a user is provided. The method includes receiving a time-varying electrical signal from an analyte sensor during a temporal phase of a monitoring session. The method includes selecting a calibration model from a plurality of calibration models, wherein the selected calibration model comprises one or more calibration model parameters. The method includes estimating at least one of the one or more calibration model parameters of the selected calibration model based on at least the time-varying electrical signal during the temporal phase of the monitoring session. The method includes estimating the blood glucose level of the user based on the selected calibration model and using the at least one estimated parameter. An apparatus and non-transitory computer readable medium having similar functionality are also provided.

48 Claims, 14 Drawing Sheets

Related U.S. Application Data

(60) Provisional application No. 62/548,328, filed on Aug. 21, 2017.

(52) U.S. Cl.
CPC .......... *A61B 5/7221* (2013.01); *A61B 5/7235* (2013.01); *A61B 2560/0223* (2013.01); *A61B 2560/0252* (2013.01); *A61B 2560/0257* (2013.01); *A61B 2562/0219* (2013.01)

(58) Field of Classification Search
CPC ... A61B 5/1495; A61B 5/7221; A61B 5/7246; A61B 5/725; A61B 5/7264; A61B 2560/0223; A61B 2560/0247; A61B 5/1455; A61B 5/14546; A61B 5/7275–7278; A61B 5/1468; A61B 5/7235; A61B 2560/0252; A61B 2560/0257; A61B 2562/0219; A61B 5/145; G16H 50/20
See application file for complete search history.

(56) References Cited

U.S. PATENT DOCUMENTS

| | | | |
|---|---|---|---|
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 9,433,376 B2* | 9/2016 | Estes | A61B 5/7203 |
| 2005/0203360 A1* | 9/2005 | Brauker | A61B 5/1451 |
| | | | 600/345 |
| 2007/0208245 A1* | 9/2007 | Brauker | A61B 5/688 |
| | | | 600/365 |
| 2008/0033254 A1* | 2/2008 | Kamath | A61B 5/725 |
| | | | 600/300 |
| 2009/0192745 A1 | 7/2009 | Kamath et al. | |
| 2011/0004085 A1* | 1/2011 | Mensinger | A61B 5/14503 |
| | | | 600/365 |
| 2011/0027127 A1 | 2/2011 | Simpson et al. | |
| 2012/0215087 A1* | 8/2012 | Cobelli | G16Z 99/00 |
| | | | 600/365 |
| 2013/0035871 A1* | 2/2013 | Mayou | G16H 50/20 |
| | | | 702/26 |
| 2013/0245981 A1 | 9/2013 | Estes et al. | |
| 2014/0051953 A1 | 2/2014 | Lamego et al. | |
| 2014/0266776 A1* | 9/2014 | Miller | A61B 5/0015 |
| | | | 340/870.01 |
| 2014/0273042 A1 | 9/2014 | Saint | |
| 2015/0282744 A1 | 10/2015 | Roy et al. | |
| 2016/0183855 A1 | 6/2016 | Vanslyke et al. | |

OTHER PUBLICATIONS

M. Vettoretti, A. Facchinetti, S. Del Favero, G. Sparacino and C. Cobelli, "Online Calibration of Glucose Sensors From the Measured Current by a Time-Varying Calibration Function and Bayesian Priors," in IEEE Transactions on Biomedical Engineering, vol. 63, No. 8, pp. 1631-1641, Aug. 2016 (Year: 2015).*

G. Acciaroli, M. Vettoretti, A. Facchinetti, G. Sparacino and C. Cobelli, "Reduction of Blood Glucose Measurements to Calibrate Subcutaneous Glucose Sensors: A Bayesian Multiday Framework," in IEEE Transactions on Biomedical Engineering, vol. 65, No. 3, pp. 587-595, Mar. 2018 (Year: 2017).*

Extended European Search Report for Application No. 18848415.8 mailed Dec. 4, 2020, 8 pages.

International Preliminary Report on Patentability for Application No. PCT/IB2018/056295 mailed Mar. 5, 2020, 7 pages.

International Search Report and Written Opinion dated Dec. 13, 2018 for Application No. PCT/IB2018/056295.

* cited by examiner

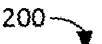
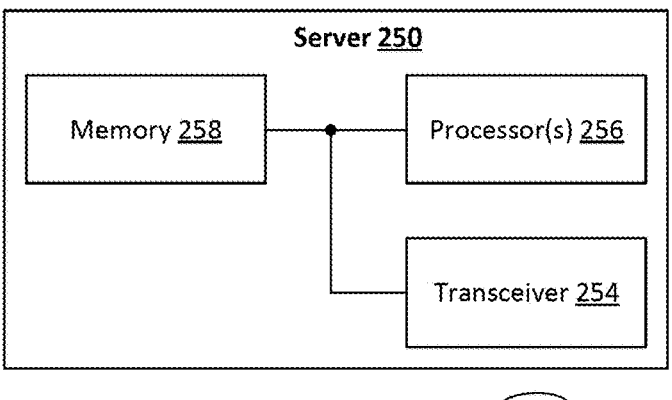
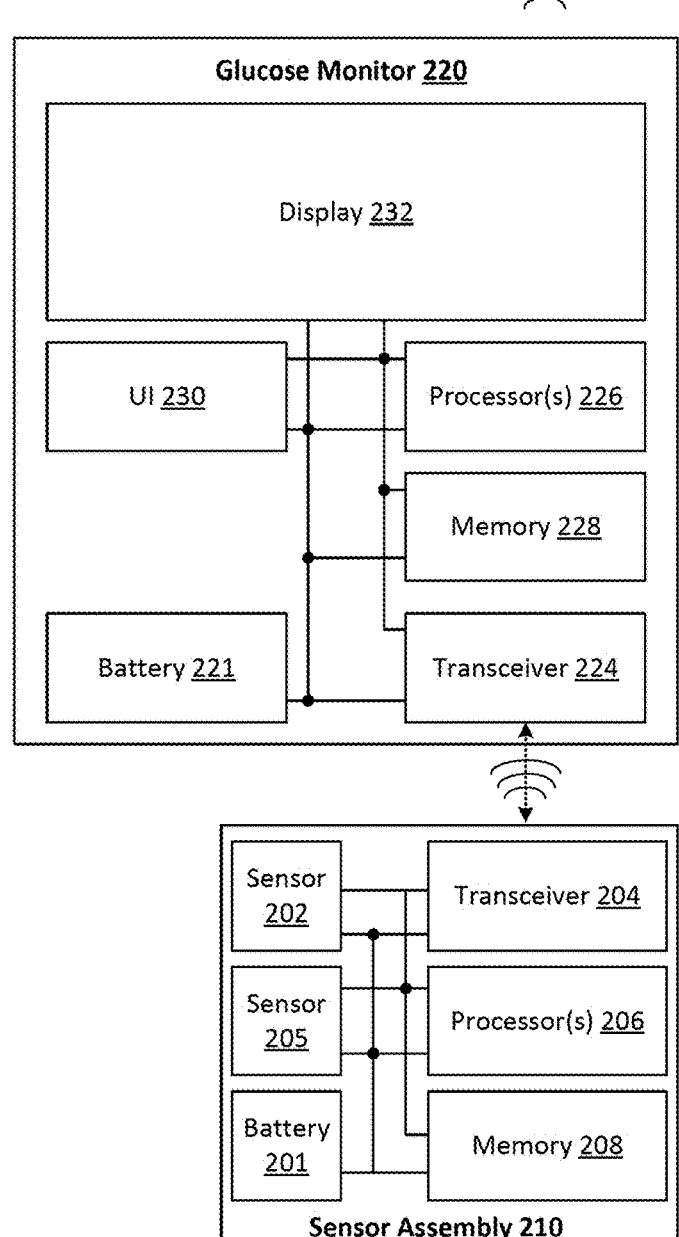
FIG. 2

800

900

1000

1100

1400

Calibration Model 1
$(\theta_1, \theta_2, \theta_3, \theta_5)$

1402

Calibration Model 2
$(\theta_2, \theta_3, \theta_5)$

1404

Calibration Model 3
$(\theta_2, \theta_3)$

1406

1500

1600

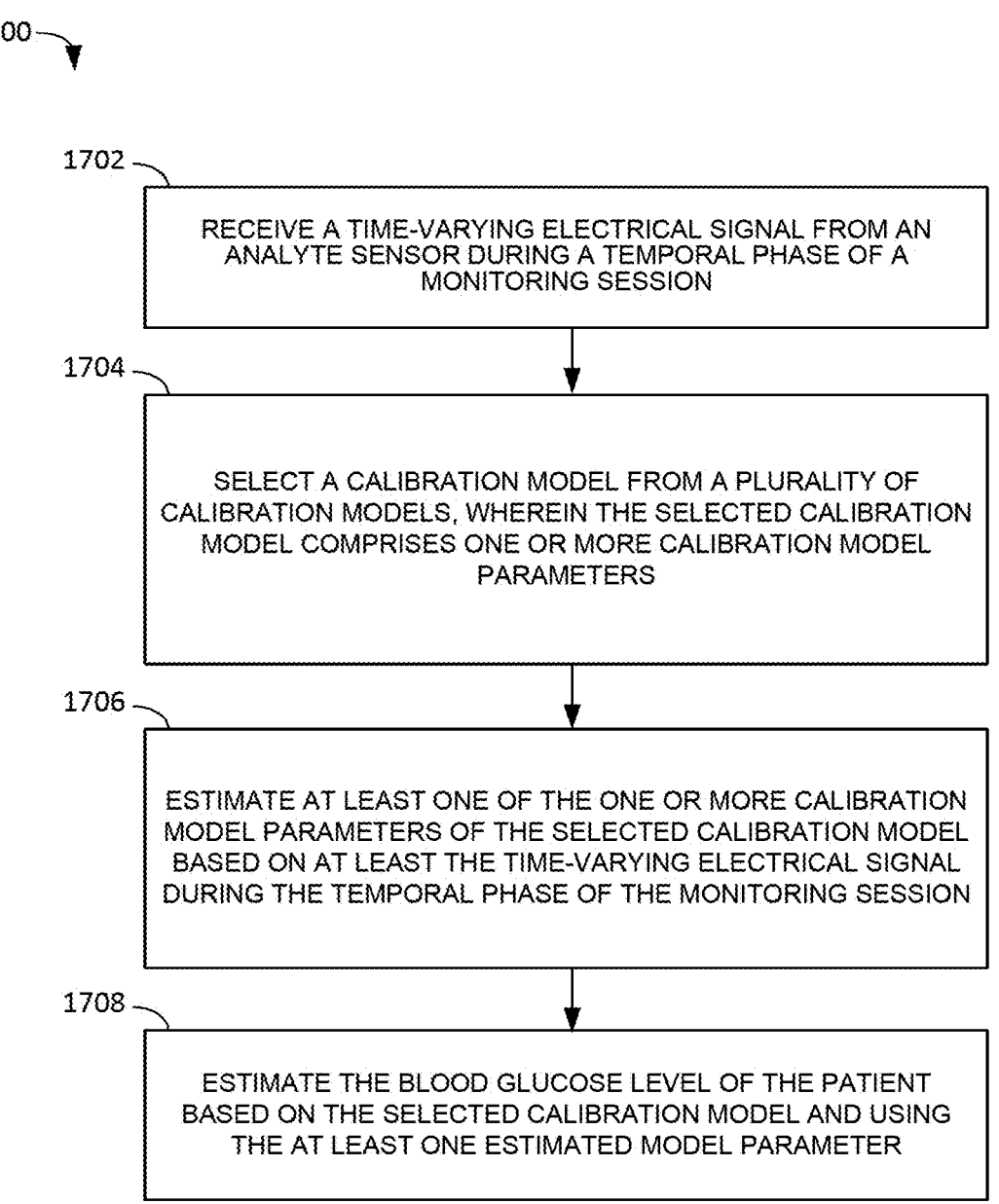

1700

1702

RECEIVE A TIME-VARYING ELECTRICAL SIGNAL FROM AN ANALYTE SENSOR DURING A TEMPORAL PHASE OF A MONITORING SESSION

1704

SELECT A CALIBRATION MODEL FROM A PLURALITY OF CALIBRATION MODELS, WHEREIN THE SELECTED CALIBRATION MODEL COMPRISES ONE OR MORE CALIBRATION MODEL PARAMETERS

1706

ESTIMATE AT LEAST ONE OF THE ONE OR MORE CALIBRATION MODEL PARAMETERS OF THE SELECTED CALIBRATION MODEL BASED ON AT LEAST THE TIME-VARYING ELECTRICAL SIGNAL DURING THE TEMPORAL PHASE OF THE MONITORING SESSION

1708

ESTIMATE THE BLOOD GLUCOSE LEVEL OF THE PATIENT BASED ON THE SELECTED CALIBRATION MODEL AND USING THE AT LEAST ONE ESTIMATED MODEL PARAMETER

CONTINUOUS GLUCOSE MONITORS AND RELATED SENSORS UTILIZING MIXED MODEL AND BAYESIAN CALIBRATION ALGORITHMS

INCORPORATION BY REFERENCE TO RELATED APPLICATION

Any and all priority claims identified in the Application Data Sheet, or any correction thereto, are hereby incorporated by reference under 37 CFR 1.57. This application is a continuation of PCT International Application No. PCT/IB2018/056295, filed Aug. 20, 2018, which designates the United States, which was published in English on Feb. 29, 2019, and which claims the benefit of U.S. Provisional Application No. 62/548,328, filed Aug. 21, 2017. Each of the aforementioned applications is incorporated by reference herein in its entirety, and each is hereby expressly made a part of this specification.

FIELD OF THE DISCLOSURE

Embodiments of continuous glucose monitors and related sensors utilizing mixed model and Bayesian calibration algorithms and associated methods of their use and/or manufacture are provided.

BACKGROUND

Diabetes mellitus is a chronic disorder of metabolism that occurs either when the pancreas is no longer able to produce insulin (Type 1 diabetes) and/or if body tissues and organs cannot effectively utilize the insulin produced (Type 2 diabetes). The lack of insulin production or an ineffective action of the available insulin causes a failure in the metabolism process, leading primarily to high values of glucose in the blood. Untreated diabetes results in both short and long term complications, such as cardiovascular and renal problems, retinopathy, neuropathy induced by hyperglycemia as well as acute adverse events related to hypoglycemia.

The standard therapy for diabetes management consists of patients acquiring measurements of self-monitoring of blood glucose samples (SMBG), by the patient by the use of lancet devices. Due to the lack of comfort associated with finger pricks, patients usually acquire only 3-4 SMBG samples per day. The few measures available do not provide a complete description of the glucose profile over time. Hyperglycemic or hypoglycemic events, occurring in the time between consecutive SMBG measurements, cannot be immediately detected, causing dangerous side effects.

A more modern device to monitor blood glucose is based on the minimally-invasive continuous glucose monitoring (CGM) sensor technology, which has become more popular and received significant clinical attention recently. This device has a sensor that is inserted subcutaneously and measures the concentration of glucose in the interstitial fluid by exploiting, for example, the glucose-oxidase enzymatic reaction. In some cases, the sensor reveals observations of a raw signal generated by the reaction on a fine, uniformly spaced, time grid, e.g. a sample every 5 min. In real-time, the device may transform these samples of electrical nature through a calibration procedure, employing a suitable mathematical model, into a time-series of blood glucose concentration levels, e.g., in milligrams per deciliter (mg/dL). A display may present these levels to the user. The mathematical model that transforms samples of an electrical signal into levels of glucose concentration has a crucial role in the accuracy of a CGM sensor. To improve effectiveness of this model during sensor functioning, calibration of its parameters can be, from time to time, estimated using SMBG values collected as reference. A typical recommended calibration frequency for the minimally-invasive sensors currently on the market is one every 12 hours. Sensor calibration is, however, of obvious discomfort and inconvenience for the patient. On the other hand, calibrations that are too temporally sparse may result in severe sensor inaccuracy and in potential threats for a patient's own safety.

SUMMARY

The present disclosure relates to systems, apparatuses and methods for measuring an analyte in a user. The various embodiments of the present systems and methods have several features, no single one of which is solely responsible for their desirable attributes.

In some embodiments, a method for monitoring a blood glucose level of a user is provided. The method includes receiving a time-varying electrical signal from an analyte sensor during a temporal phase of a monitoring session. The method includes selecting a calibration model from a plurality of calibration models, wherein the selected calibration model comprises one or more calibration model parameters. The method includes estimating at least one of the one or more calibration model parameters of the selected calibration model based on at least the time-varying electrical signal during the temporal phase of the monitoring session. The method includes estimating the blood glucose level of the user based on the selected calibration model and using the at least one estimated parameter.

In some embodiments, the method further includes receiving a reference input. In some embodiments, selecting the calibration model is based at least in part on the selected calibration model having the highest probability, of the plurality of candidate calibration models, of predicting an actual blood glucose level of the user utilizing the time-varying electrical signal. In some embodiments, the probability is a Bayesian probability. In some embodiments, selecting the calibration model is further based at least in part on detecting a pattern corresponding to the selected calibration model in the time-varying electrical signal. In some embodiments, the temporal phase is defined to span a respective predefined interval of time. In some embodiments, at least one of a start and an end of the temporal phase is determined based on occurrence of corresponding patterns in the time-varying electrical signal. In some embodiments, one of the corresponding patterns is a noise component of the time-varying electrical signal satisfying a threshold.

In some embodiments, estimating at least one of the one or more calibration model parameters of the selected calibration model comprises: setting the one or more calibration model parameters to an initial value, transforming the time-varying electrical signal into an estimated interstitial glucose level of the user utilizing the selected calibration model and the initial value of the one or more calibration model parameters, estimating the blood glucose level based on the estimated interstitial glucose level, updating the one or more calibration model parameters based on a difference between the estimated blood glucose level and a reference input of the blood glucose level of the user, and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

In some embodiments, the predefined relationship comprises at least one of the estimated interstitial glucose level and the estimated blood glucose level being within a predetermined accuracy of the reference input of the blood glucose level. In some embodiments, the initial value of the one or more calibration model parameters is a prior average value for the one or more calibration model parameters. In some embodiments, the plurality of candidate calibration models comprise a common global calibration model, each utilizing one or more unique calibration model parameters. In some embodiments, the global calibration model comprises a first portion corresponding to a baseline behavior of the analyte sensor and a second portion corresponding to a sensitivity of the analyte sensor. In some embodiments, time-varying electrical signal comprises a plurality of sensor data points. In some embodiments, the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

In some embodiments, an apparatus configured to monitor a blood glucose level of a user is provided. The apparatus includes a memory, and a processor configured to receive a time-varying electrical signal from an analyte sensor during a temporal phase of a monitoring session. The processor is further configured to select a calibration model from a plurality of calibration models, wherein the selected calibration model comprises one or more calibration model parameters. The processor is further configured to estimate at least one of the one or more calibration model parameters of the selected calibration model based on at least the time-varying electrical signal and the reference input during the temporal phase of the monitoring session. The processor is further configured to estimate the blood glucose level of the user based on the selected calibration model and using the at least one estimated parameter.

In some embodiments, the apparatus further includes the analyte sensor. In some embodiments, the processor is further configured to receive a reference input. In some embodiments, the processor is configured to select the calibration model based at least in part on the selected calibration model having the highest probability, of the plurality of candidate calibration models, of predicting an actual blood glucose level of the user utilizing the time-varying electrical signal. In some embodiments, the probability is a Bayesian probability. In some embodiments, the processor is configured to select the calibration model based at least in part on detecting a pattern corresponding to the selected calibration model in the time-varying electrical signal. In some embodiments, the temporal phase is defined to span a respective predefined interval of time. In some embodiments, the processor is configured to determine at least one of a start and an end of the temporal phase based on occurrence of corresponding patterns in the time-varying electrical signal. In some embodiments, one of the corresponding patterns is a noise component of the time-varying electrical signal satisfying a threshold.

In some embodiments, the processor is configured to estimate at least one of the one or more calibration model parameters of the selected calibration model by setting the one or more calibration model parameters to an initial value, transforming the time-varying electrical signal into an estimated interstitial glucose level of the user utilizing the selected calibration model and the initial value of the one or more calibration model parameters, estimating the blood glucose level based on the estimated interstitial glucose level, updating the one or more calibration model parameters based on a difference between the estimated blood glucose level and a reference input of the blood glucose level of the user, and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

In some embodiments, the predefined relationship comprises at least one of the estimated interstitial glucose level and the estimated blood glucose level being within a predetermined accuracy of the reference input of the blood glucose level. In some embodiments, the initial value of the one or more calibration model parameters is a prior average value for the one or more calibration model parameters. In some embodiments, the plurality of candidate calibration models comprise a common global calibration model, each utilizing one or more unique calibration model parameters. In some embodiments, the global calibration model comprises a first portion corresponding to a baseline behavior of the analyte sensor and a second portion corresponding to a sensitivity of the analyte sensor. In some embodiments, the time-varying electrical signal comprises a plurality of sensor data points. In some embodiments, the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

In some embodiments, a non-transitory, computer-readable medium comprising code is provided. The code, when executed, causes a processor of an apparatus configured to monitor a blood glucose level of a user to receive a time-varying electrical signal from an analyte sensor during a temporal phase of a monitoring session. The code, when executed, further causes the processor to select a calibration model from a plurality of calibration models, wherein the selected calibration model comprises one or more calibration model parameters. The code, when executed, further causes the processor to estimate at least one of the one or more calibration model parameters of the selected calibration model based on at least the time-varying electrical signal and the reference input during the temporal phase of the monitoring session. The code, when executed, further causes the processor to estimate the blood glucose level of the user based on the selected calibration model and using the at least one estimated parameter.

In some embodiments, the code, when executed, further causes the processor to receive a reference input. In some embodiments, selecting the calibration model is based at least in part on the selected calibration model having the highest probability, of the plurality of candidate calibration models, of predicting an actual blood glucose level of the user utilizing the time-varying electrical signal. In some embodiments, the probability is a Bayesian probability. In some embodiments, selecting the calibration model is further based at least in part on detecting a pattern corresponding to the selected calibration model in the time-varying electrical signal. In some embodiments, the temporal phase is defined to span a respective predefined interval of time. In some embodiments, at least one of a start and an end of the temporal phase is determined based on occurrence of corresponding patterns in the time-varying electrical signal. In some embodiments, one of the corresponding patterns is a noise component of the time-varying electrical signal satisfying a threshold.

In some embodiments, estimating at least one of the one or more calibration model parameters of the selected calibration model includes the processor: setting the one or more calibration model parameters to an initial value, transforming the time-varying electrical signal into an estimated interstitial glucose level of the user utilizing the selected calibration model and the initial value of the one or more calibration model parameters, estimating the blood glucose level based on the estimated interstitial glucose level, updating the one or more calibration model parameters based on a difference between the estimated blood glucose level and a reference input of the blood glucose level of the user, and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

In some embodiments, the predefined relationship comprises at least one of the estimated interstitial glucose level and the estimated blood glucose level being within a predetermined accuracy of the reference input of the blood glucose level. In some embodiments, the initial value of the one or more calibration model parameters is a prior average value for the one or more calibration model parameters. In some embodiments, the plurality of candidate calibration models comprise a common global calibration model, each utilizing one or more unique calibration model parameters. In some embodiments, the global calibration model comprises a first portion corresponding to a baseline behavior of the analyte sensor and a second portion corresponding to a sensitivity of the analyte sensor. In some embodiments, the time-varying electrical signal comprises a plurality of sensor data points. In some embodiments, the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout the depicted embodiments.

FIG. 2 illustrates a box diagram of several components of the continuous analyte sensor system of FIG. 1, in accordance with some embodiments.

FIG. 17 illustrates a flowchart of a method for monitoring a blood glucose level of a user, in accordance with some embodiments.

DETAILED DESCRIPTION

The following description and examples illustrate some example embodiments in detail. Those of skill in the art will recognize that there are numerous variations and modifications of the disclosed embodiments that are encompassed by its scope. Accordingly, the description of a certain example embodiment should not be deemed to limit the scope of the present disclosure.

The present application is directed to embodiments of continuous glucose monitors and related sensors utilizing mixed model and Bayesian calibration algorithms and associated methods of their use and manufacture. As will be described in more detail in connection with the figures below, certain features of the described monitors, sensors, and calibration methods provide novel and inventive solutions to problems associated with previous monitor, sensor and calibration designs and methods or their use or manufacture.

System Introduction

Figure 1:
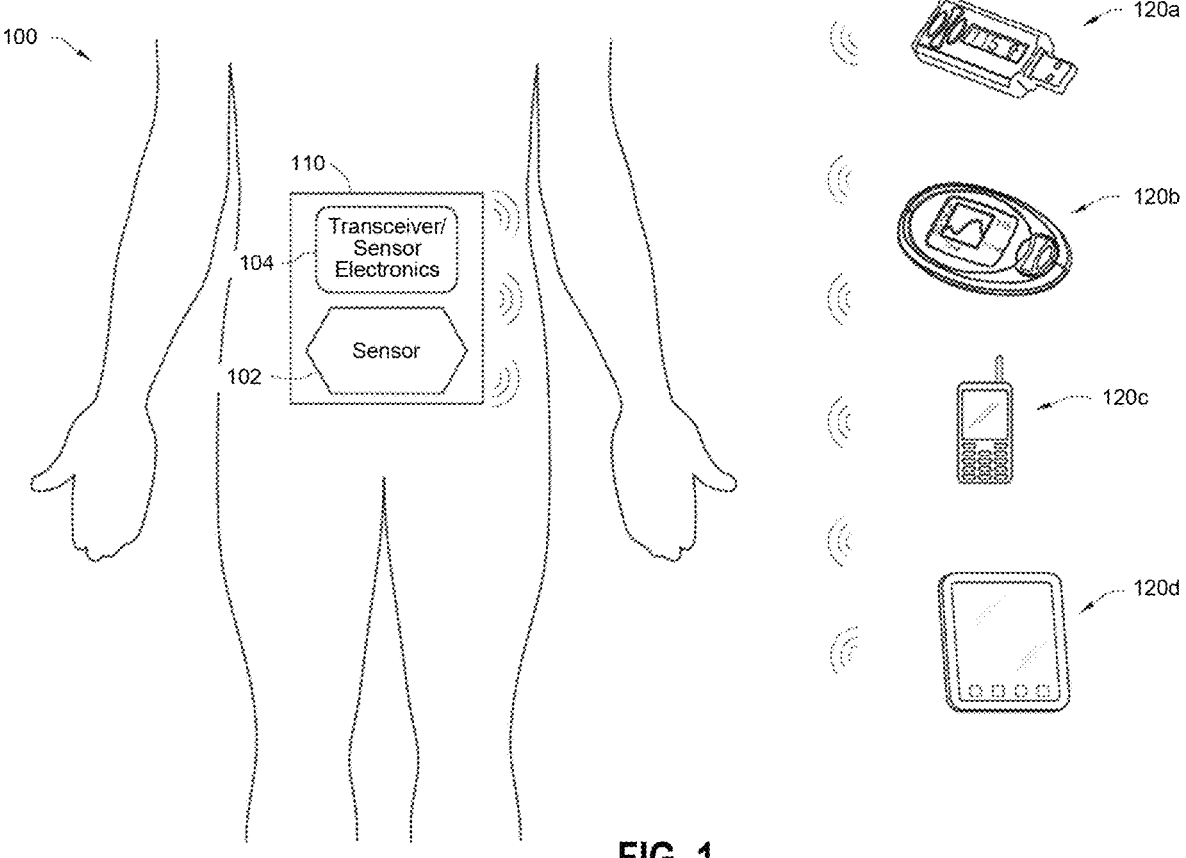
FIG. 1 illustrates a schematic view of a continuous analyte sensor system, in accordance with some embodiments.

FIG. 1 is a schematic of a continuous analyte sensor system 100 attached to a user (e.g., a person). The analyte sensor system 100 may include an on-skin sensor assembly 110 configured to communicate with a monitor 120a-120d (which may be located remotely from the user). The on-skin sensor assembly 106 is fastened to the skin of a user via a base (not shown), which may be a disposable housing.

The system 100 includes a transcutaneous analyte sensor 102 and an electronics unit (referred to interchangeably as sensor electronics, transceiver or transmitter) 104 for wirelessly transmitting analyte information to a receiver (e.g., a transceiver) within the monitor 120a-120d (not shown in FIG. 1). The term transceiver may be considered to include either or both of a transmitter configured to transmit a signal and a receiver configured to receive a signal. In some embodiments, the monitor 120a-120d includes a display screen, which can display information to a person such as the user. Example monitors include computers such as dedicated display devices, mobile electronics, smartphones, smartwatches, tablet computers, laptop computers, and desktop computers. In some embodiments, Apple Watches, iPhones, and iPads made by Apple Inc., may function as the monitor. Monitors may be running customized or stock operating systems such as, but not limited to, Linux, iOS by Apple Inc., Android by Google Inc., or Windows by Microsoft.

In some embodiments, the monitor 120a-120d is mechanically coupled to the electronics unit 104 to enable the monitor 120a-120d to receive data (e.g., analyte data) from the electronics unit 104. To increase the convenience to users, in several embodiments, the monitor 120a-120d does not need to be mechanically coupled to the electronics unit 104 and can even receive data wirelessly from the electronics unit 104 over great distances (e.g., when the receiver is many feet or even many miles from the electronics unit 104).

During use, a sensing portion of the sensor 102 can be under the user's skin and a contact portion of the sensor 102 can be electrically connected to the electronics unit 104. The electronics unit 104 can be engaged with a housing (e.g., a base) or directly coupled to an adhesive patch fastened to the skin of the user.

The on-skin sensor assembly 110 may be attached to the user with use of an applicator adapted to provide convenient and secure application. Such an applicator may also be used for attaching the electronics unit 104 to a base, inserting the sensor 102 through the user's skin, and/or connecting the sensor 102 to the electronics unit 104. Once the electronics unit 104 is engaged with the base and the sensor 102 has been inserted into the skin (and is connected to the electronics unit 104), the sensor assembly can detach from the applicator.

The continuous analyte sensor system 100 can include a sensor configuration that provides an output signal indicative of a concentration of an analyte. The output signal (e.g., sensor data, such as a raw data stream, filtered data, smoothed data, and/or otherwise transformed sensor data) is sent to the monitor 120a-120d.

In some embodiments, the analyte sensor system 100 includes a transcutaneous glucose sensor, such as is described in U.S. Patent Publication No. US-2011-0027127-A1, the entire contents of which are hereby incorporated by reference. In some embodiments, the sensor system 100 includes a continuous glucose sensor and comprises a transcutaneous sensor (e.g., as described in U.S. Pat. No. 6,565,509, as described in U.S. Pat. No. 6,579,690, as described in U.S. Pat. No. 6,484,046). The contents of U.S. Pat. Nos. 6,565,509, 6,579,690, and 6,484,046 are hereby incorporated by reference in their entirety.

In several embodiments, the sensor system 100 includes a continuous glucose sensor and comprises a refillable subcutaneous sensor (e.g., as described in U.S. Pat. No. 6,512,939). In some embodiments, the sensor system 100 includes a continuous glucose sensor and comprises an intravascular sensor (e.g., as described in U.S. Pat. No. 6,477,395, as described in U.S. Pat. No. 6,424,847). The contents of U.S. Pat. Nos. 6,512,939, 6,477,395, and 6,424,847 are hereby incorporated by reference in their entirety.

Various signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entirety. The sensor can extend through a housing, which can maintain the sensor on the skin and can provide for electrical connection of the sensor to sensor electronics, which can be provided in the electronics unit 104.

One or more repeaters, receivers and/or display devices, such as a key fob repeater, a medical device receiver (e.g., an insulin delivery device and/or a dedicated glucose sensor receiver), a smartphone, a portable computer, and the like can be communicatively coupled to the electronics unit 104 (e.g., to receive data from the electronics unit 104). The electronics unit 104 can also be referred to as a transmitter. In some embodiments, the monitor 120a-120d transmits data to the electronics unit 104. The sensor data can be transmitted from the sensor electronics unit 104 to one or more of the key fob repeater, the medical device receiver, the smartphone, the portable computer, and the like. In some embodiments, analyte values are displayed on a display device of the monitor 120a-120d.

The electronics unit 104 may communicate with the monitor 120a-120d, and/or any number of additional devices, via any suitable communication protocol. Example communication protocols include radio frequency; Bluetooth; universal serial bus; any of the wireless local area network (WLAN) communication standards, including the IEEE 802.11, 802.15, 802.20, 802.22 and other 802 communication protocols; ZigBee; wireless (e.g., cellular) telecommunication; paging network communication; magnetic induction; satellite data communication; and/or a proprietary communication protocol.

Any sensor shown or described herein can be an analyte sensor; a glucose sensor; and/or any other suitable sensor. A sensor described in the context of any embodiment can be any sensor described herein or incorporated by reference, such as an analyte sensor; a glucose sensor; any sensor described herein; and any sensor incorporated by reference.

Sensors shown or described herein can be configured to sense, measure, detect, and/or interact with any analyte.

As used herein, the term analyte is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products.

In some embodiments, the analyte for measurement by the sensing regions, devices, systems, and methods is glucose. However, other analytes are contemplated as well, including, but not limited to ketone bodies; Acetyl Co A; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; cortisol; testosterone; choline; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba* histolytic a, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); acetone (e.g., succinylacetone); acetoacetic acid; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and intermediaries in the Citric Acid Cycle.

The terms continuous analyte sensor, and continuous glucose sensor, as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (e.g., by continuously or continually adjusting or determining the sensor's sensitivity and background), for example, at time intervals ranging from fractions of a second up to, for example, 1, 2, or 5 minutes, or longer.

The terms raw data stream and data stream, as used herein, are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or current) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The terms sensor data and sensor signal as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream of analog or digital signals directly related to a measured analyte from an analyte sensor (or other signal received from another sensor), as well as calibrated and/or filtered raw data. In one example, the sensor data or sensor signal comprises digital data in counts converted by an A/D converter from an analog signal (e.g., voltage or current) and includes one or more data points representative of a glucose concentration. Thus, the terms sensor data point and data point refer generally to a digital representation of sensor data at a particular time. The terms broadly encompass a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data or sensor signal includes an integrated digital value representative of one or more data points averaged over a time period. Sensor data may include calibrated data, smoothed data, filtered data, transformed data, and/or any other data associated with a sensor.

FIG. 2 illustrates a box diagram 200 of several components of the continuous analyte sensor system of FIG. 1, in accordance with some embodiments. The analyte sensor system may comprise a sensor assembly 210 and a glucose monitor 220, substantially corresponding to the sensor assembly 110 and the monitor 120a-120d previously described in connection with FIG. 1. In some embodiments, the analyte sensor system may further include a server 250 configured to provide offline computing and/or provision of data utilized in calibrating blood glucose readings by monitor 220 and sensor assembly 210.

Sensor assembly 210 may comprise a sensor 202, a transceiver 204 (e.g., transmitter) a processor 206, a memory 208, and a power source (e.g., battery) 201. The sensor 202 and transceiver 204 may correspond substantially to the sensor 102 and transceiver 104, respectively, of FIG. 1. The sensor 202 may be configured to sense a level of one or more analytes on or within the user, to generate a signal (e.g., continuous or discrete electrical current or electrical voltage or discrete communications thereof) indicative of the level of the one or more analytes, and to provide the signal to transceiver 204 and/or to processor 206. In some embodiments, processor 206 may be configured to process the raw signal from sensor 202. Transceiver 204 may be configured to communicate the raw signal from sensor 202 to glucose monitor 220 or to communicate the processed signal from processor 206 and/or memory 208 to glucose monitor 220. Such communication may be either wired or wireless, as indicated by the dotted double sided arrow and wave-like lines, respectively. The battery 201 may be configured to supply operational power to transceiver 204, processor 206, memory 208 and/or sensor 202.

In some embodiments, sensor assembly 210 may further include a sensor 205 configured to receive power from battery 201 and to measure at least one of an acceleration of the user, a temperature, a galvanic response, an impedance of the sensor and/or tissue, a second electrochemical sensor, an atmospheric pressure, or any other physical property that may be subsequently utilized in calibration of a sensor signal from sensor 202. In such embodiments, sensor 205 may either provide a raw sensor signal to transceiver 204 for communication to glucose monitor 220 or to processor 206 and/or memory 208 for processing before communication to glucose monitor 220 via transceiver 204.

Glucose monitor 220 may comprise a transceiver 224 (e.g., transmitter and/or receiver) configured to communicate at least with sensor assembly 210, for example, receiving a time-varying sensor signal, or an indication thereof, from sensor assembly 210. Monitor 220 further comprises one or more processors 226 and a memory 228 configured to process the sensor signal as described below. Monitor 220 may further comprise a user interface (UI) 230 configured to receive input from the user, for example, one or more blood glucose reference measurements. Monitor 220 may further comprise a display 232 configured to present information to the user, for example, estimated blood glucose levels of the user. In some embodiments, display 232 may be a part of UI 230. Monitor 220 may further comprise a battery 221 configured to provide electrical power to any of transceiver 224, memory 228, processor(s) 226, UI 230, display 232 or any other portion of monitor 220.

As will be described in more detail below, in some embodiments, one or more parameters, variables or probabilities for calibrating blood glucose measurements may be determined offline (e.g., by a separate server 250) and communicated to monitor 220. Likewise, where substantial calibrating computations are utilized, such computations, or portions thereof, may be performed by server 250 after pertinent data is communicated from monitor 220 to server 250, and the result may be communicated from server 250 to monitor 220. In this way, monitor 220 may leverage an increased processing capability provided by server 250 and thereby reduce a requirement for computational power in monitor 220 itself. Accordingly, in some embodiments, server 250 may comprise a transceiver 254 configured to communicate with monitor 220 via transceiver 224. Server 250 may further comprise one or more processors 256 and a memory 258 configured to determine one or more parameters, variables or probabilities for calibrating blood glucose measurements offline, as will be described in more detail below, and communicate the one or more parameters, variables, probabilities or any other data to monitor 220 via transceiver 254 at server 250 and transceiver 244 at monitor 220.

Calibration Model Introduction

A continuous glucose monitoring (CGM) device typically includes an electrochemical needle sensor placed subcutaneously in the abdomen or in the arm. This sensor periodically measures (e.g., every 1-5 minutes) a current or voltage signal generated by the glucose-oxidase reaction and thus related to the glucose concentration in the interstitial fluid. The raw current or voltage signal is converted into an interstitial glucose (IG) concentration and then into a blood glucose concentration utilizing transformation algorithms or conversion functions whose parameters are estimated by a calibration procedure that, in some embodiments, exploits self-monitored blood glucose (SMBG) samples and/or other reference inputs. The output value for blood glucose levels that results from the calibration process may then be displayed to the user in real-time with almost continuous-time glucose measurements, usually expressed in milligrams per deciliter (mg/dL).

The variability of the relation between sensor current and IG concentration typically requires CGM sensors to be periodically recalibrated, for example every 12 hours, in order to preserve sensor accuracy. While not wanting to be bound by theory, principal causes of inaccuracy are, if not properly compensated, the blood glucose (BG) to interstitial glucose (IG) kinetics, the variability of sensor sensitivity and baseline, and the noise affecting the measurements.

Several algorithms that directly process the raw current signal and exploit frequent BG references have been proposed with the aim of mitigating calibration error. Recently, Bayesian strategies have been utilized to estimate calibration function parameters, exploiting approximately two calibrations per day and improving accuracy compared to manufacturer calibration. Further improvements in day one accuracy, and consequently in global sensor performance, have been obtained by using, for the calibration function parameters, Bayesian priors specifically derived from the first twelve hours of monitoring. This Bayesian approach provides not only improved accuracy but also reduced frequency of calibrations from two to one per day with consequent reduction of user discomfort associated with SMBG sample collection.

Although these Bayesian approaches show promising results, further reduction of calibrations, which is desirable for both ease-of-use and cost-of-use, has not been achievable with previously proposed calibration models at least because models that utilize linear approximations of the time-varying relation between sensor current and IG concentrations limits their domain of validity to short time windows between blood glucose calibrations. To overcome these limitations and further reduce the frequency of calibrations, a global model valid for the entire monitoring session is desirable. A monitoring session may be defined as a continuous period during which an analyte concentration, e.g., glucose concentration, is monitored by a particular sensor.

The present application presents a new calibration methodology, based on a global calibration model that is defined for the entire monitoring session, which processes the raw current or voltage signal and calibration inputs that can include one or more BG references, additional sensors, and/or signal metrics in real-time and outputs the calibrated IG profile utilizing a Bayesian statistical framework. In particular, according to some embodiments, a calibration model based on the global calibration model, but utilizing a set of calibration model parameters unique to the calibration model, is selected from a predefined set of candidate calibration models. The selection is based on the selected calibration model having a highest a priori probability of accurately predicting blood glucose levels that match received references of measured blood glucose, utilizing at least an analyte sensor signal as an input to the model. Statistical expectations are available on probabilities relating to each candidate model, to the unknown model parameters of each candidate model, and to the time-variability of each candidate model as the sensor ages through its usable life.

A global model is used because sensor properties, such as sensitivity and baseline generally evolve continuously over the sensor session. For example, a global model could describe sensor sensitivity with a mathematical function that characterizes the typical time required to reach a stable value when a new sensor is inserted under the skin. Within this global model framework there might be several candidate models to describe sensor aging. For example, a first model could have a function describing the behavior observed in the majority of subject where the sensor equilibrates to a stable value. A second model, could have additional mathematical equations or adjustable parameters to describe sensors with slowly declining sensitivity at the end of the use period that might occur less frequently or only in a small fraction of subjects.

Considering that the time-varying nature of sensor characteristics shows different patterns throughout a given monitoring session, in some embodiments the specific set of candidate calibration models may be different for different temporal phases of the continuous glucose monitoring (CGM) session, e.g., a beginning phase, a middle phase, and an ending phase. For example, some baseline-related factors may have more influence at the beginning of the monitoring session than at the end, thus requiring the definition of specific models, based on the global calibration model, in the candidates for the beginning phase. Yet other sensitivity-related factors may influence the likelihood of the estimations more at the end of the session than at the beginning, with the consequent introduction of specific models, based on the global calibration model, in the candidates for the end phase. In some embodiments, a middle phase may be characterized by a simpler model, in which some calibration factors related to aspects of a beginning phase or of an ending phase of a monitoring session could be ignored or given a reduced weight.

In some embodiments, a change in a device-physiology interface state may be determined by estimating a confidence in each model correctly describing a current state of an analyte sensor, where each temporal phase of the monitoring session may be associated with one or more different interface states. The device-physiology interface state depends on the local physiology surrounding the sensor and can change due to sensor insertion trauma, foreign body response, and wound healing in ways that include changes in blood flow and tissue composition. In some cases, the sensor calibration can be changed due to fouling of the membrane surface or changes in the relationship between interstitial glucose and blood glucose. A transition from one such state to another may be identified by one candidate calibration model becoming more likely than another to accurately describe the current state of the analyte sensor based on one or more real-time inputs, as guided by a statistical knowledge of how similar sensors behave under similar conditions. Identification of such transitions may be accomplished utilizing a statistical test rather than a set of heuristic rules or thresholds. Thus, the teachings of the present application go beyond merely compensating for sensor manufacturing differences, but further account for sensor properties including: sensitivity, baseline, and noise as they change through the lifetime of the sensor(s).

Accordingly, some embodiments of the calibration process proceed as follows. Every time a new blood glucose reference value, e.g., a self-measured blood glucose (SMBG) reference from a finger stick, is available for calibration, a Bayesian statistical framework is utilized to select one calibration model from among a set of candidate calibration models associated with or utilizable for the current phase of the monitoring session. The different candidate models are treated as competing hypotheses. Applying the Bayesian approach to hypothesis testing, the probability that a particular calibration model will accurately predict at least the new blood glucose reference (but also all previous blood glucose references in some embodiments) utilizing at least an analyte sensor signal as an input to the model is represented by statistical models. Bayes' theorem is then used to obtain the posterior probability for each candidate calibration model. In particular, the integrated likelihood of a match is computed for each candidate calibration model associated with or utilizable for the current phase of a monitoring session by carrying out asymptotic calculations through, for example, Monte Carlo simulation methods. Once a calibration model has been selected, unknown model parameters for the selected calibration model may be determined by means of a Bayesian estimation procedure that exploits a priori statistical knowledge of each parameter derived from an independent training set, and non-parametric deconvolution that compensates for the BG-to-IG kinetics In other embodiments, the hypothesis testing step and resulting model selection can also be triggered by changes in the sensor signal characteristics including noise magnitude, frequency content, or other aspects of its statistical distribution or time series. These signal-based metrics can indicate changes in the device-physiology interface or aging of the sensor that can be used to evaluate the best candidate model. These sensor signal based metrics can be used alone or in combination with the blood glucose calibrations. Several aspects of the calibration methodology will now be described in more detail.

Global Calibration Model

According to some embodiments, a calibration model having a set of calibration model parameters processes or transforms a sensor signal $y_f(t)$ (e.g., an electrical current or voltage) provided by a sensor (e.g., sensor 102, 202 of FIGS. 1 and 2) to obtain an estimated IG profile $u_I(t)$ utilizing SMBG references $u_B(t)$ acquired by finger prick devices or any other method of blood glucose reference acquisition. The two input measures (the sensor signal $y_f(t)$ and the SMBG samples $u_B(t)$) belong to different physical domains, e.g. the current or voltage domain and the glucose domain, as well as to different physiological sites. For example, SMBG measurements are acquired in the blood, while the sensor current is measured in the interstitial fluid. Thus, to calibrate the sensor signal $y_f(t)$ exploiting BG references $u_B(t)$, a global calibration model describing the relation between the sensor signal $y_f(t)$ and the SMBG samples $u_B(t)$ may be used.

Figure 3:
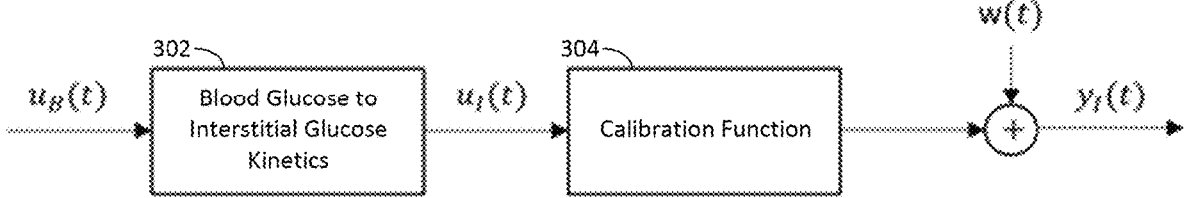
FIG. 3 illustrates a box diagram of a model for illustrating a relation between a sensor signal and self-monitored blood glucose samples, in accordance with some embodiments.

A schematic representation of a suitable conceptual model for illustrating the relation between a sensor signal $y_f(t)$ and SMBG samples $u_B(t)$ is shown in FIG. 3. Modeling how a blood glucose profile $u_B(t)$ translates to a sensor signal profile $y_f(t)$ may be conceptualized as a two-step process. First, block 302 considers the relationship between a blood glucose profile $u_B(t)$ and an interstitial glucose (IG) profile $u_I(t)$, according to the first-order differential equation Eq. 1:

$$\tau \cdot \frac{d}{dt} u_I(t) = -u_I(t) + u_B(t) \qquad \text{(Eq. 1)}$$

where the variable $\tau$, expected to show variability between subjects, is the diffusion time-constant between plasma and interstitium.

Accordingly, it can be shown that the IG profile $u_I(t)$ is the output of a first-order linear dynamic system, having the BG profile $u_B(t)$ as input and an impulse response $h(t)$, given by Eq. 2.

$$h(t) = \frac{1}{\tau} e^{-\frac{t}{\tau}} \qquad \text{(Eq. 2)}$$

$h(t)$ has a low-pass filtering effect, imparting both amplitude attenuation and phase delay, thereby causing $u_I(t)$ to be a distorted version of $u_B(t)$. Accordingly, the IG profile $u_I(t)$ can be described as a convolution of the BG profile $u_B(t)$ with impulse response $h(t)$, according to Eq. 3, where $\otimes$ indicates a convolution operation:

$$u_I(t) = u_B(t) \otimes \frac{1}{\tau} e^{-\frac{t}{\tau}} \qquad \text{(Eq. 3)}$$

Next, with reference to FIG. 3, block 304 represents a calibration function that receives the IG profile $u_I(t)$ as an input and outputs the sensor signal $y_f(t)$, which is derived from the sensor measuring IG, corrupted by additive noise $w(t)$, described by Eq. 4:

$$y_I(t) = [u_I(t) + b(t)] \cdot s(t) + w(t) \qquad \text{(Eq. 4)}$$

where $w(t)$ is a noise profile, $b(t)$ is a baseline profile of the glucose profile, and $s(t)$ is a sensitivity of the sensor.

In comparison with previous calibration approaches, where the calibration models have domains of validity restricted to the time windows between consecutive calibrations, the domain of validity of Eq. 4 is the entire monitoring session. Accordingly, Eq. 4 provides a global calibration model that is valid across the entire monitoring session from which candidate calibration models may be derived.

Working in reverse from the two step model of FIG. 3, estimating the BG profile $u_B(t)$ from the sensor signal $y_f(t)$ may also be conceptualized as a two-step process: firstly estimating the IG profile $u_I(t)$ from the sensor signal $y_f(t)$, and secondly, estimating the BG profile $u_B(t)$ from the estimated IG profile $u_I(t)$.

Regarding the first step, solving Eq. 4 for the IG profile $u_I(t)$ and neglecting the noise profile $w(t)$ results in Eq. 5:

$$u_I(t) = \frac{y_I(t)}{s(t)} - b(t) \qquad \text{(Eq. 5)}$$

Regarding the second step, solving Eq. 3 for blood glucose profile $u_B(t)$ includes deconvolution of the IG profile $u_I(t)$ with the impulse function $h(t)$ of Eq. 2.

Calibration Models Based on the Global Calibration Model

As shown by Eq. 5, the actual interstitial glucose profile $u_I(t)$ as a function of the sensor signal $y_f(t)$ depends on at least the baseline profile $b(t)$ and the sensor sensitivity profile $s(t)$, which are not necessarily static functions across an entire monitoring session.

Accordingly, different temporal intervals, or phases, of a monitoring session may be defined by at least different sensitivity and baseline behaviors, each of which may be described or predicted accurately utilizing different sets of candidate calibration models best suited for a particular phase or state of a monitoring session, wherein each candidate calibration model is based on the global calibration model of Eqs. 4 and 5, however, incorporating unique baseline profiles $b(t)$ and/or sensor sensitivity profiles $s(t)$.

Figure 4:
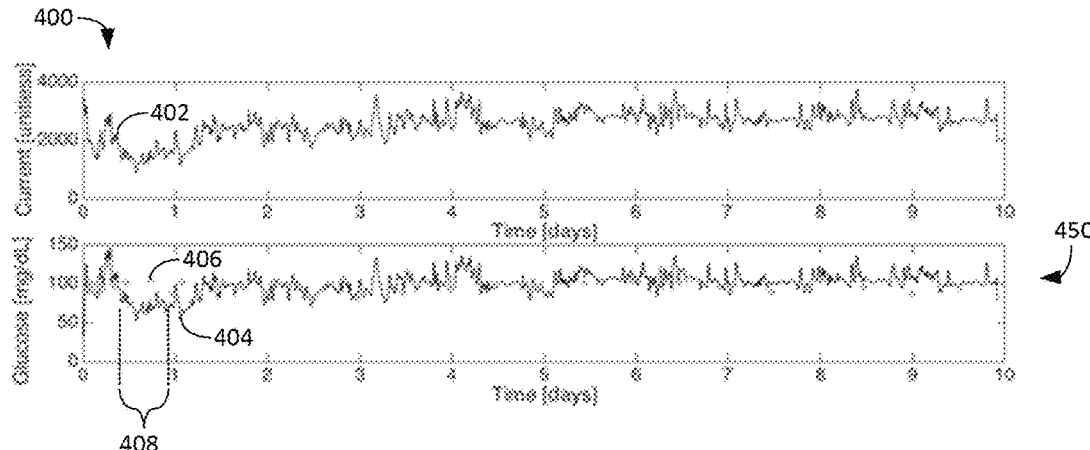
FIG. 4 illustrates a beginning-phase component in a sensor signal, in accordance with some embodiments.

For example, FIG. 4 illustrates a beginning-phase component in a sensor signal, in accordance with some embodiments. Graph 400 illustrates a sensor signal 402 over the course of a monitoring session depicted as lasting ten days. Graph 450 illustrates a blood glucose level 404 estimated utilizing a static calibration algorithm based on sensor signal 402 as an input. A negative drop in sensor signal 402 around the first day of monitoring is not congruent with SMBG reference measurements 406 during interval 408, and results in large errors in estimated blood glucose level 404, compared to SMBG reference measurements 406 during interval 408. Such behaviors, for instance, may be related to signal artifacts occurring due to an immune system response or other components occurring in the first days after sensor insertion. Accordingly, a set of candidate calibration models associated with a beginning phase of a monitoring session may each include a different formulation of the baseline profile b (t) describing and accounting for one of, for example: no negative drop in the sensor signal $y_f(t)$, a moderate negative drop of approximately a first amount in the sensor signal $y_f(t)$, and a severe negative drop of approximately a second amount greater than the first amount in the sensor signal $y_f(t)$ during at least a portion of a beginning phase of a monitoring session. The calibration model most accurately describing the behavior of the particular sensor signal $y_f(t)$ being calibrated may then be selected based on a Bayesian statistical framework.

An example baseline profile b(t) for candidate calibration models may take several forms depending on the type of analyte sensor used, the insertion mechanism, and the formation device-physiology interface state. In some cases, the baseline has a steady value that can be quantified in terms of it equivalent analyte concentration (for example +5 mg/dL or −5 mg/dL) for the entire duration. In another case the baseline has a steady value that can be quantified in terms of it equivalent analyte signal (for example +50 pico amperes (pA) or −50 pA) for the entire duration. In cases the magnitude of the baseline varies over time, either increasing or decreasing, and can be modeled a variety of functions, including, but not limited to, a linear function (including a constant function), logarithmic function, quadratic function, cubic function, square root function, power function, polynomial function, rational function, exponential function, sinusoidal function, and variations and combinations thereof.

In other case, the baseline profile b(t) may have periods of time where it drops or dips below its typical value followed by a period of time where it returns to the typical value. One example is the form of Eq. 6. However, the present concepts are not so limited and the baseline profile b(t), including profiles accounting for negative drops in the sensor signal $y_f(t)$, may take any appropriate form.

$$b(t) = b_0 \cdot e^{-\mu t} - \rho \cdot e^{-\eta t} + b_f \qquad \text{(Eq. 6)}$$

where $\mu$, $\eta$, and $\rho$ are fixed values, where $\mu$ and $\eta$ represent exponential decay constants that model the time course (such that small values represent slow changes in the signal over time), where $\rho$ represents the relative contribution of the two time profiles, and $b_0$, and $b_f$ are model parameters, where $b_0$ represents an initial baseline condition (that may occur when a sensor is initially inserted into the tissue) and $b_f$ represents a final condition (when the device-physiology interface state has stabilized).

Similarly, the end phase of a monitoring session may be characterized by specific time-varying components, e.g., loss of sensor sensitivity.

Figure 5:
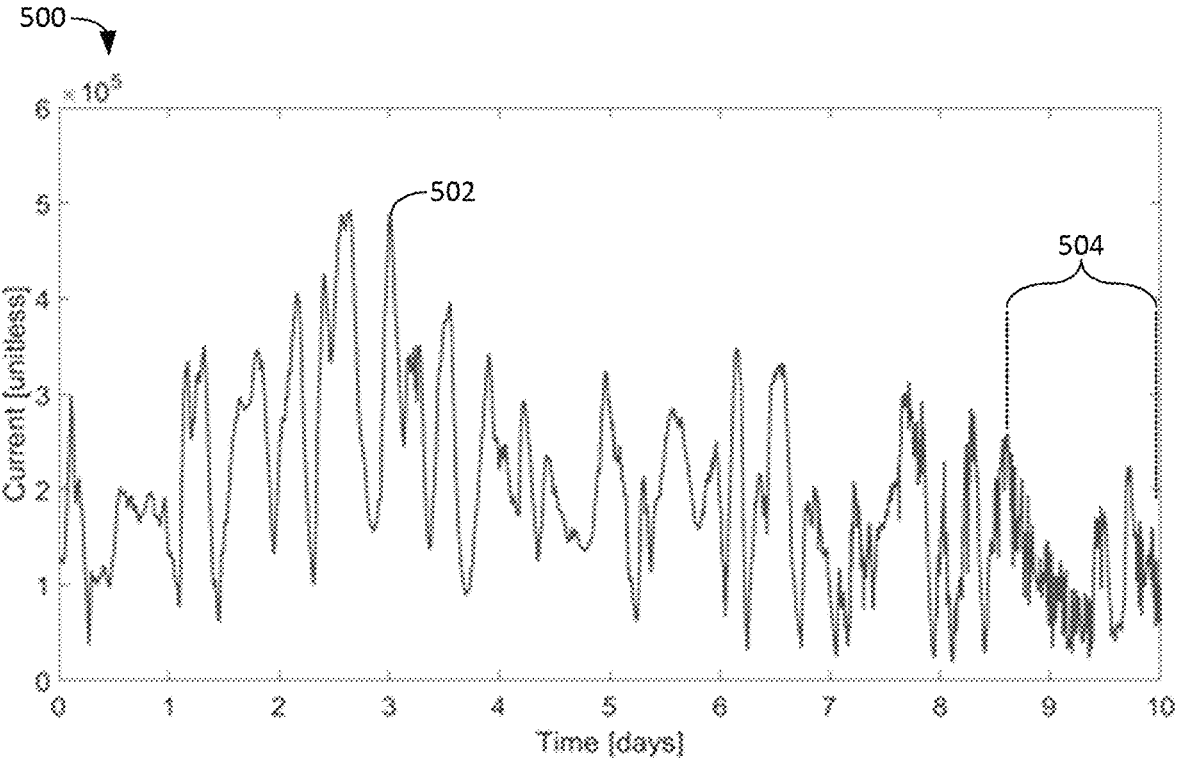
FIG. 5 illustrates an end-phase component in a sensor signal, in accordance with some embodiments.

FIG. 5 illustrates an end-phase component in a sensor signal, in accordance with some embodiments. Graph 500 illustrates a sensor signal 502 produced where sensor sensitivity declines in the last days of monitoring, as shown for interval 504. Such a decline in sensor sensitivity leads to a decrease in amplitude in sensor signal 502, and a subsequent underestimation of the blood glucose level when utilizing a static calibration algorithm that uses sensor signal 502 as an input. Accordingly, a set of candidate calibration models associated with an ending phase of a monitoring session may each include a different formulation of the sensitivity profile s(t) describing and accounting for different levels of sensor sensitivity decline.

Example sensor sensitivity profiles s(t) of different candidate calibration models for the ending phase may have the generic form given by any one of Eqs. 7-9, illustrating an example bi-exponential profile, mono-exponential profile, and linear profile, respectively. However, the present concepts are not so limited and the sensor sensitivity profile s(t) may take any appropriate form.

$$s_1(t) = m_0 \cdot \left\{ 1 + \frac{m_f - m_0}{m_0} \cdot \left[ r \cdot (1 - e^{-\alpha t}) + (1 - r) \cdot \left( 1 - e^{-\beta t} \right) \right] \right\} \qquad \text{(Eq. 7)}$$

$$s_2(t) = m_0 \cdot \left[ 1 + \frac{m_f - m_0}{m_0} \cdot (1 - e^{-\alpha t}) \right] \qquad \text{(Eq. 8)}$$

$$s_3(t) = m_0 + \frac{(m_f - m_0)}{T} t \qquad \text{(Eq. 9)}$$

where $\alpha$, $\beta$, r, T are constant values represent exponential decay constants that model the time course of the sensor equilibration, and $m_0$ and $m_f$ are calibration model parameters ($m_0$ represents an initial sensitivity condition that may occur when a sensor is initially inserted into the tissue and $m_f$ represents a final condition) that must be subsequently determined.

In some embodiments, switching between the different candidate calibration models could be based on time by determining the time-phases in which the different calibration factors act. For example, a beginning phase may be defined to begin at the beginning of a monitoring session and extend for a first predetermined interval of time. A middle phase may be defined to begin at the end of the beginning phase and to extend for a second predetermined interval of time. Such a middle phase could be characterized by calibration factors having a substantial effect during the middle phase, while aspects substantially affecting only the beginning phase or the ending phase of the monitoring session could be neglected. An ending phase may be defined to begin at the end of the middle phase and to extend for a third predetermined interval of time, ending at the end of the monitoring session.

In some other embodiments, the switching between candidate calibration models may be based at least in part on detecting patterns in the sensor signal $y_f(t)$, e.g., noise levels or dips or surges in the sensor signal satisfying a predefined shape, pattern, frequency, duration or threshold, and/or from any other information derived from the calibration model itself.

Relative Effects of Calibration Model Parameters During Respective Phases

In some embodiments, candidate calibration models specific for each phase of the monitoring session, derived from a global calibration model, may consider only the calibration model parameters that substantially affect the calibration during the respective phase for which the candidate calibration model is most accurate.

In some embodiments, the baseline profile b(t) of Eqs. 4 and 5 may be described by the form given by Eq. 10:

$$b(t) = \theta_1 b_\alpha(t) + \theta_2 \qquad \text{(Eq. 10)}$$

where $\theta_1$ and $\theta_2$ are calibration model parameters to be subsequently determined, and $b_\alpha(t)$ is any fixed functions of time weighted by $\theta_1$.

Where multiple candidate calibration models consider baseline profile b(t) in a particular phase of the monitoring session, each candidate calibration model may utilize different parameters $\theta_1$ and $\theta_2$ and/or a different fixed function $b_\alpha(t)$.

In some embodiments, the sensor sensitivity profile s(t) may have the generic form described by Eq. 11:

$$s(t) = \theta_3 s_\alpha(t) + \theta_4 s_\beta(t) + \theta_5 \qquad \text{(Eq. 11)}$$

where $s_\alpha(t)$ and $s_\beta(t)$ are fixed functions of time whose formulations may be sensor specific and may be determined accordingly to the manufacturer, and $\theta_3$, $\theta_4$, and $\theta_5$ are calibration model parameters to be subsequently determined, subject to the constraints of Eq. 12 and Eq. 13, where $\varphi$ has a fixed value:

$$\theta_3, \theta_4, \theta_5 > 0 \qquad \text{(Eq. 12)}$$

$$\frac{\theta_3}{\theta_4} = \varphi \qquad \text{(Eq. 13)}$$

Where multiple candidate calibration models consider sensitivity profile s(t) in a particular phase of the monitoring session, each candidate calibration model may utilize different parameters $\theta_3$, $\theta_4$, $\theta_5$ and/or different fixed functions $s_\alpha(t)$ and $s_\beta(t)$.

Accordingly, from Eqs. 10-13 and the dependence between sensitivity parameters ($\theta_3=\varphi\cdot\theta_4$), the final parameters vector, i.e., the collection of calibration model parameters, for subsequent determination, of a candidate calibration model may be given by Eq. 14:

$$\theta = [\theta_1, \theta_2, \theta_3, \theta_5]^T \qquad \text{(Eq. 14)}$$

As shown by Eq. 13, because $\theta_4$ depends directly from $\theta_3$, $\theta_4$ need not be included in the parameters vector $\theta$. In some embodiments, starting from the global model of Eqs. 4 and 5 defined on the entire monitoring session, the relative impact of each calibration model parameter $\theta_1$, $\theta_2$, $\theta_3$, $\theta_5$ on the estimated glucose values in different phases of the monitoring session may be determined. On the basis of this determination, different candidate calibration models, derived from the initial global calibration model of Eqs. 4 and 5, are defined for each temporal phase. The calibration process may select, for each calibration, the appropriate candidate calibration model, estimating only the calibration model parameters useful to explain the specific dynamic of the sensor signal $y_f(t)$ in the considered phase.

The relative contribution of each of the calibration parameters $\theta_1$, $\theta_2$, $\theta_3$, $\theta_5$ over time may be assessed by simulating, from the raw sensor signal $y_f(t)$, different calibrated profiles as functions of a single one of the parameters, keeping constant the other parameters. Based on Eqs. 5 and 10-13, the related calibrated IG profile may be given by Eq. 15:

$$u_I(t, \theta_1, \theta_2, \theta_3, \theta_5) = \frac{y_I(t)}{s(t, \theta_3, \theta_5)} - b(t, \theta_1, \theta_2) \qquad \text{(Eq. 15)}$$

Thus, the influence of each calibration model parameter on the estimated interstitial glucose profile $u_I(t)$ may be assessed by varying its value over a meaningful range, while fixing the other calibration model parameters to constant values. Each calibration model parameter is analyzed, individually, in the following sections.

Parameter $\theta_1$

The estimated interstitial glucose profile $u_I(t, \theta_1)$, as a function of time t and parameter $p_1$, is obtained from the sensor signal $y_I(t)$ utilizing Eq. 16:

$$u_I(t, \theta_1) = \frac{y_I(t)}{s(t)} - b(t, \theta_1) \qquad \text{(Eq. 16)}$$

where all other model parameters, $\theta_2$, $\theta_3$, $\theta_4$, $\theta_5$, are fixed to any meaningful value in the range of their prior distributions, e.g., to the mean value of their prior distributions.

Figure 6:
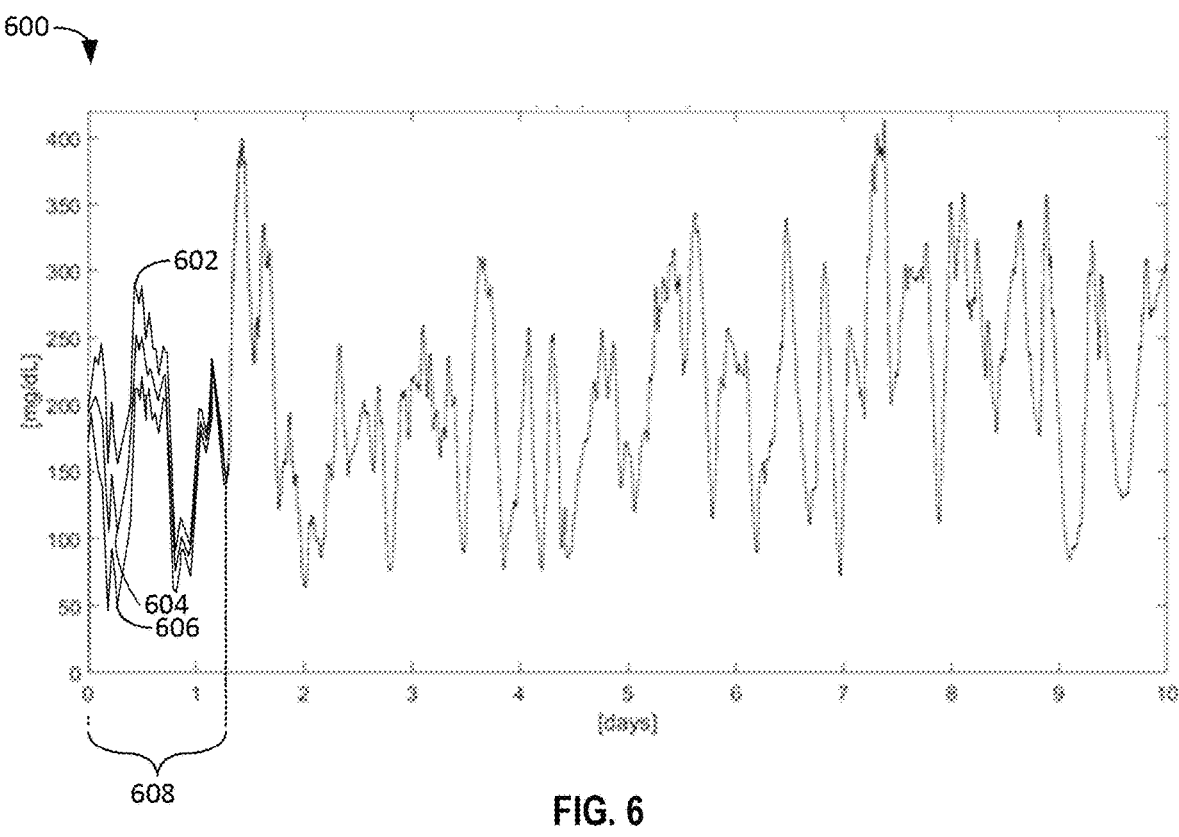
FIG. 6 illustrates an effect that a first calibration model parameter has on an estimation of blood glucose levels of a user, in accordance with some embodiments.

An example simulation of Eq. 16 is shown in FIG. 6, which illustrates an effect 600 of the calibration model parameter $\theta_1$ on estimated blood glucose levels $u_I(t, \theta_1)$ of a user. Calibration model parameter $\theta_1$ is varied through its domain of validity and the variability bands at the $5^{th}$ and $95^{th}$ percentile 606, 602, respectively, are reported together with the mean profile 604. FIG. 6 illustrates that the estimated glucose profile $u_I(t)$ substantially depends on calibration model parameter $\theta_1$ only in the first two days, during interval 608, while almost no influence is evident after day two.

Figure 7:
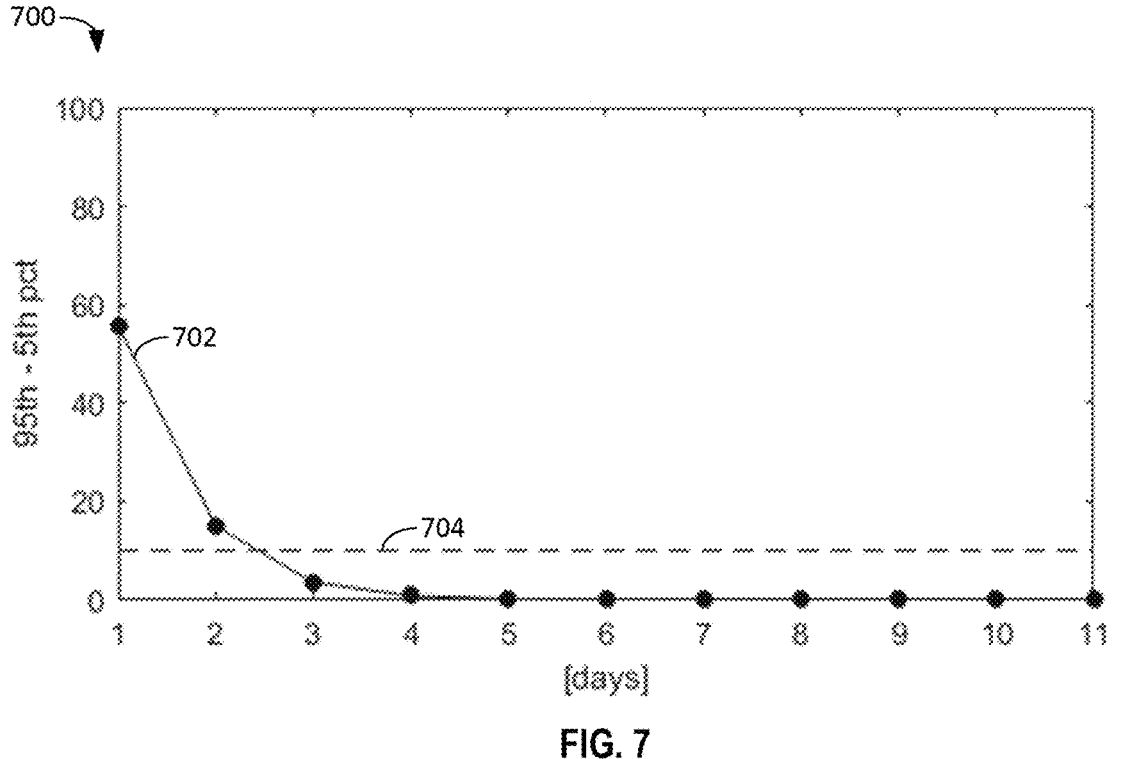
FIG. 7 illustrates a difference between the $5^{th}$ and $95^{th}$ percentile of the effect of the first calibration model parameter on the estimated blood glucose levels of the user as shown in FIG. 6.

FIG. 7 illustrates a difference 702 between the $5^{th}$ and $95^{th}$ percentile 606, 602 of the effect of the calibration model parameter $\theta_1$ on the estimated blood glucose levels $u_I(t)$ of the user as shown in FIG. 6. A threshold 704 of a 10 mg/dl difference in estimated blood glucose levels between the $5^{th}$ and $95^{th}$ percentile 606, 602 is shown, indicating a predetermined threshold below which the calibration model parameter $\theta_1$ may be determined not to have a substantial effect on the estimated blood glucose levels $u_I(t)$. However, the predetermined threshold of 10 mg/dl is exemplary and not limiting. Any higher or lower predetermined threshold value may be utilized. Accordingly, this simulation indicates that the calibration model parameter $\theta_1$ has a substantial effect on the estimated blood glucose levels $u_I(t)$ during the first 2-3 days.

Parameter $\theta_2$

The estimated glucose profile $u_I(t, \theta_2)$, as a function of time t and parameter $\theta_2$, is obtained from the signal $y_I(t)$ utilizing Eq. 17:

$$u_I(t, \theta_2) = \frac{y_I(t)}{s(t)} - b(t, \theta_2) \qquad \text{(Eq. 17)}$$

where all other model parameters, $\theta_1$, $\theta_3$, $\theta_4$, $\theta_5$ are fixed to any meaningful value in the range of their prior distributions, e.g., to the mean value of their prior distributions.

Figure 8:
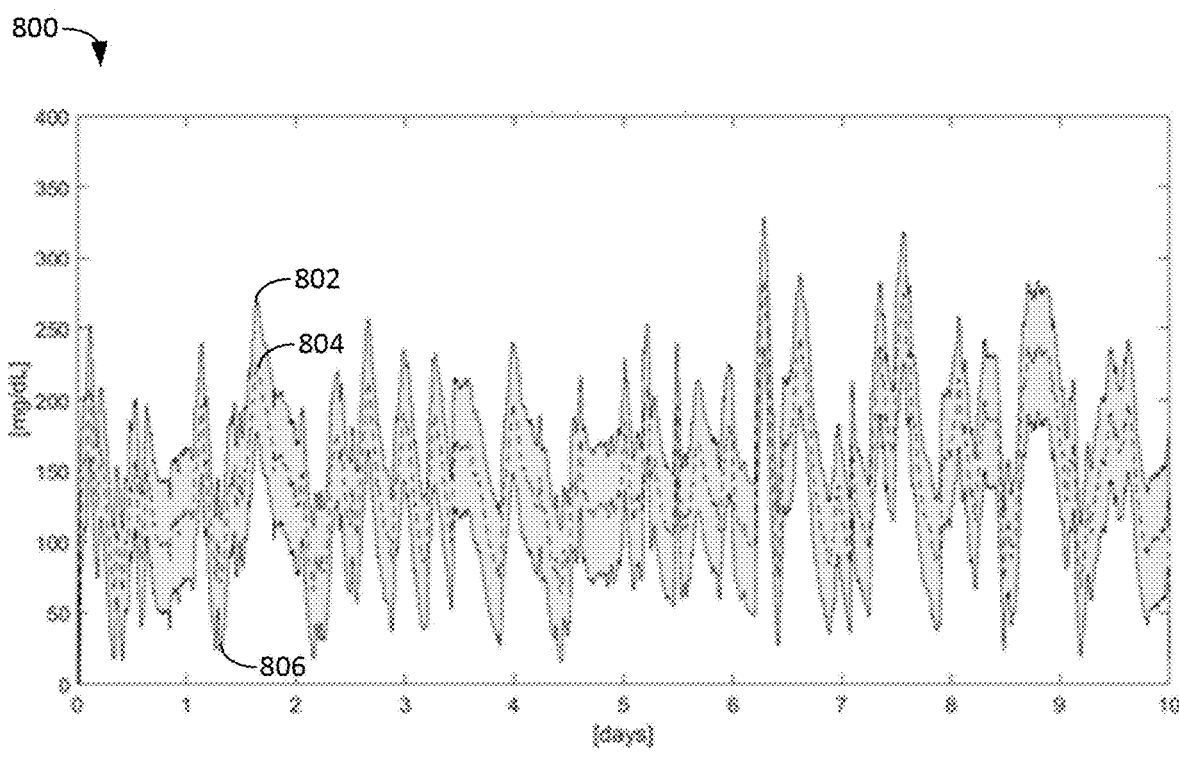
FIG. 8 illustrates an effect that a second calibration model parameter has on an estimation of blood glucose levels of a user, in accordance with some embodiments.

An example simulation of Eq. 17 is shown in FIG. 8, which illustrates an effect 800 of the calibration model parameter $\theta_2$ on estimated blood glucose levels $u_I(t, \theta_2)$ of a user. Calibration model parameter $\theta_2$ is varied through its domain of validity and the variability bands at the $5^{th}$ and $95^{th}$ percentile 806, 802, respectively, are reported together with the mean profile 804. FIG. 8 illustrates that the estimated glucose profile $u_I(t)$ substantially depends on calibration model parameter $\theta_2$ across the entire monitoring session.

Figure 9:
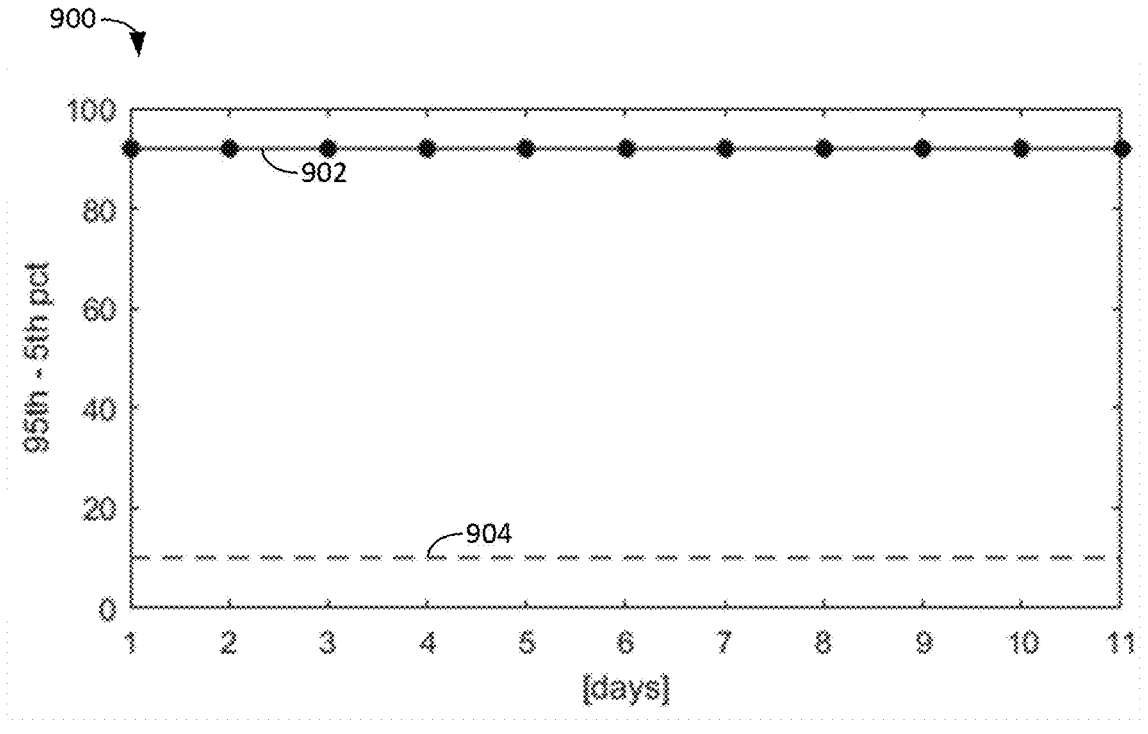
FIG. 9 illustrates a difference between the $5^{th}$ and $95^{th}$ percentile of the effect of the second calibration model parameter on the estimated blood glucose levels of the user as shown in FIG. 8.

FIG. 9 illustrates a difference 902 between the $5^{th}$ and $95^{th}$ percentile 806, 802 of the effect of the calibration model parameter $\theta_2$ on the estimated blood glucose levels $u_I(t)$ of the user as shown in FIG. 8. A threshold 904 of a 10 mg/dl difference in estimated blood glucose levels between the $5^{th}$ and $95^{th}$ percentile 806, 802 is shown, indicating a predetermined threshold below which the calibration model parameter $\theta_2$ may be determined not to have a substantial effect on the estimated blood glucose levels $u_f(t)$. However, the predetermined threshold of 10 mg/dl is exemplary and not limiting. Any predetermined threshold value may be utilized. Accordingly, this simulation indicates that the calibration model parameter $\theta_2$ has a substantial effect on the estimated blood glucose levels $u_f(t)$ during the entire monitoring session.

Parameter $\theta_3$

The estimated glucose profile $u_f(t, \theta_3)$, as a function of time t and parameter $p_3$, is obtained from the raw signal $y_f(t)$ utilizing Eq. 18:

$$u_I(t, \theta_3) = \frac{y_I(t)}{s(t)} - b(t, \theta_3) \qquad \text{(Eq. 18)}$$

where all other model parameters, $\theta_1$, $\theta_2$, $\theta_4$, $\theta_5$ are fixed to any meaningful value in the range of their prior distributions, e.g., to the mean value of their prior distributions.

Figure 10:
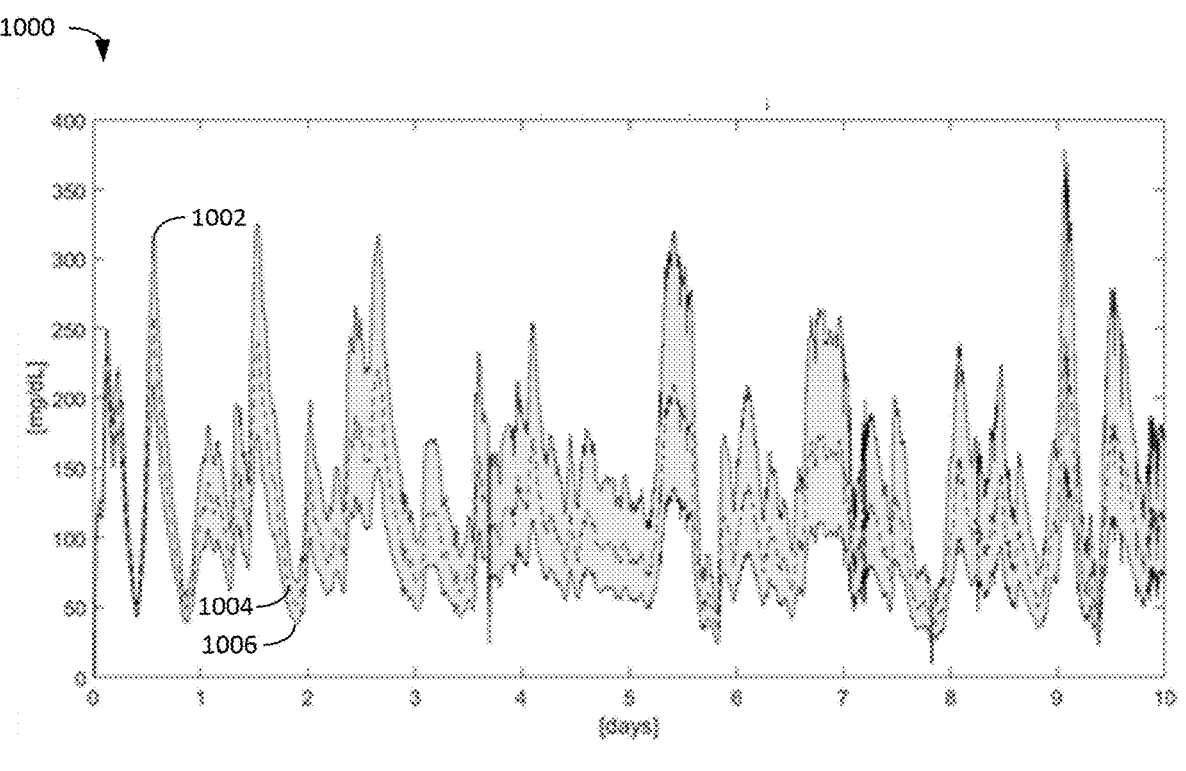
FIG. 10 illustrates an effect that a third calibration model parameter has on an estimation of blood glucose levels of a user, in accordance with some embodiments.

An example simulation of Eq. 18 is shown in FIG. 10, which illustrates an effect 1000 of the calibration model parameter $\theta_3$ on estimated blood glucose levels $u_f(t, \theta_3)$ of a user. Calibration model parameter $\theta_3$ is varied through its domain of validity and the variability bands at the $5^{th}$ and $95^{th}$ percentile 1006, 1002, respectively, are reported together with the mean profile 1004. FIG. 10 illustrates that the estimated glucose profile $u_f(t)$ substantially depends on calibration model parameter $\theta_3$ across the entire monitoring session. However, noting that the influence of calibration model parameter $\theta_3$ on the calibration process is more evident at the end of the monitoring session than at the beginning.

Figure 11:
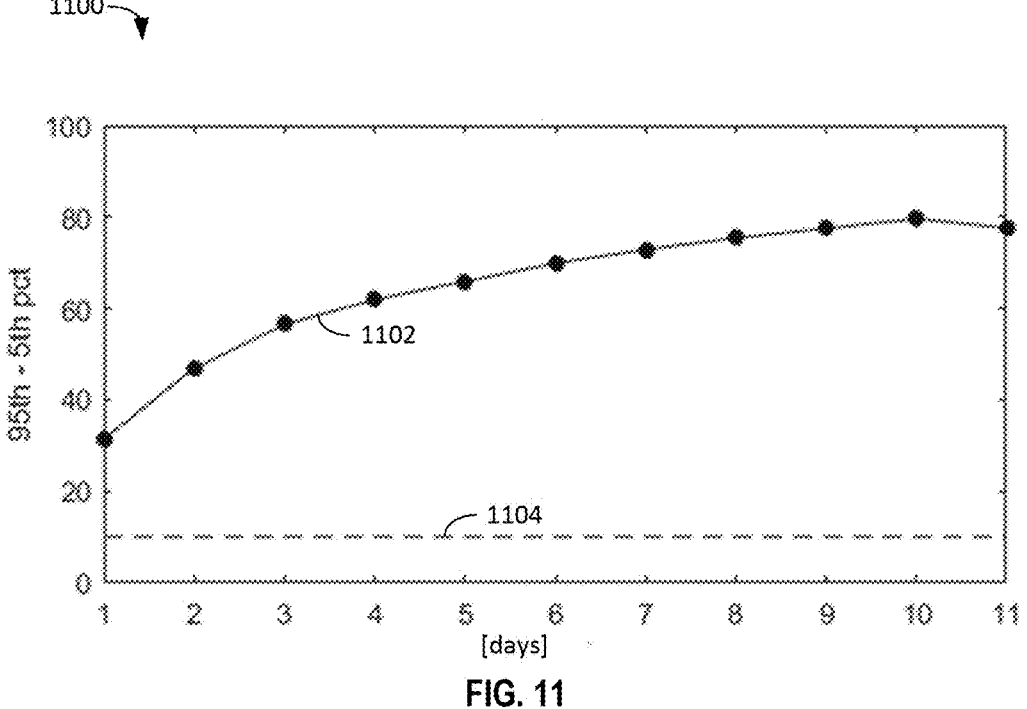
FIG. 11 illustrates a difference between the $5^{th}$ and $95^{th}$ percentile of the effect of the third calibration model parameter on the estimated blood glucose levels of the user as shown in FIG. 10.

FIG. 11 illustrates a difference 1102 between the $5^{th}$ and $95^{th}$ percentile 1006, 1002 of the effect of the calibration model parameter $\theta_3$ on the estimated blood glucose levels $u_f(t)$ of the user as shown in FIG. 10. A threshold 1104 of a 10 mg/dl difference in estimated blood glucose levels between the $5^{th}$ and $95^{th}$ percentile 1006, 1002 is shown, indicating a predetermined threshold below which the calibration model parameter $\theta_3$ may be determined not to have a substantial effect on the estimated blood glucose levels $u_f(t)$. However, the predetermined threshold of 10 mg/dl is exemplary and not limiting. Any predetermined threshold value may be utilized. Accordingly, this simulation indicates that the calibration model parameter $p_3$ has a substantial effect on the estimated blood glucose levels $u_I$ (t) during the entire monitoring session and particularly at the end of the monitoring session.

Parameter $\theta_5$

The estimated interstitial glucose profile $u_f(t, \theta_5)$, as a function of time t and parameter $\theta_5$, is obtained from the raw sensor signal $y_f(t)$ utilizing Eq. 19:

$$u_I(t, \theta_5) = \frac{y_I(t)}{s(t)} - b(t, \theta_5) \qquad \text{(Eq. 19)}$$

where all other model parameters, $\theta_2$, $\theta_3$, $\theta_4$, $\theta_5$, are fixed to any meaningful value in the range of their prior distributions, e.g., to the mean value of their prior distributions.

Figure 12:
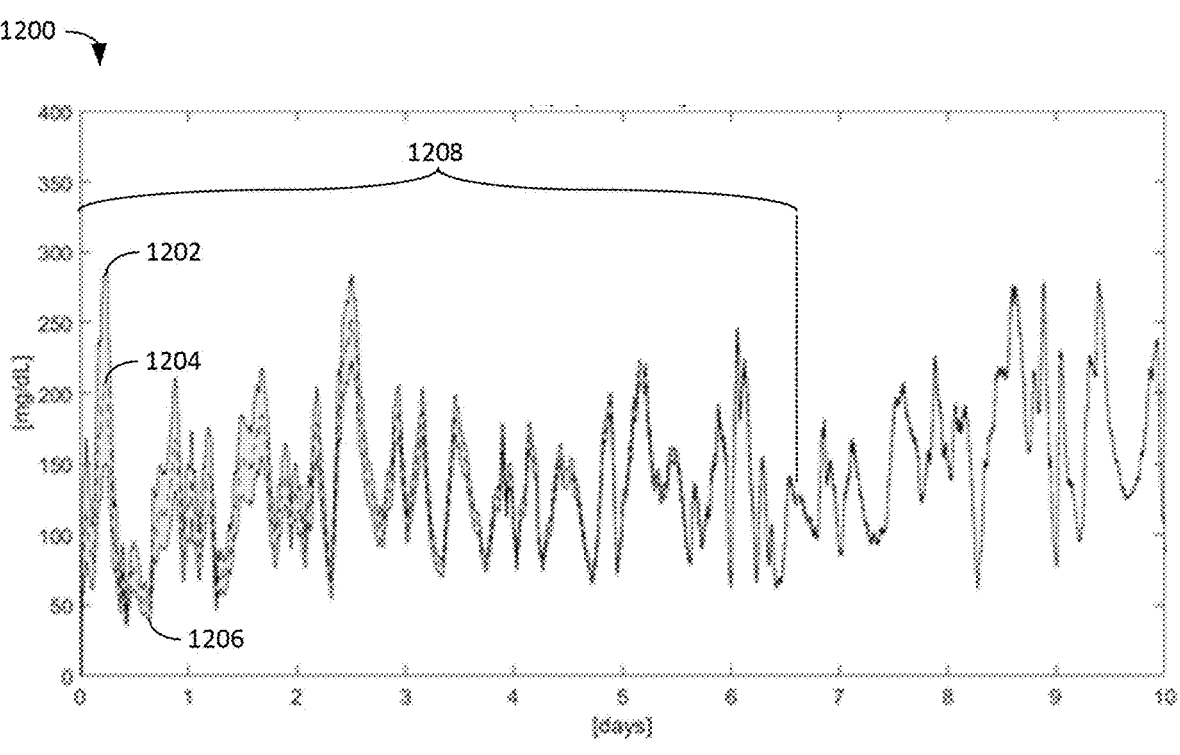
FIG. 12 illustrates an effect that a fifth calibration model parameter has on an estimation of blood glucose levels of a user, in accordance with some embodiments.

An example simulation of Eq. 19 is shown in FIG. 12, which illustrates an effect 1200 of the calibration model parameter $\theta_5$ on estimated blood glucose levels $u_f(t, \theta_5)$ of a user. Calibration model parameter $\theta_5$ is varied through its domain of validity and the variability bands at the $5^{th}$ and $95^{th}$ percentile 1205, 1202, respectively, are reported together with the mean profile 1204. FIG. 12 illustrates that the estimated glucose profile $u_f(t)$ substantially depends on calibration model parameter $\theta_5$ during approximately the first seven days, during interval 1208, while almost no influence is evident after day seven.

Figure 13:
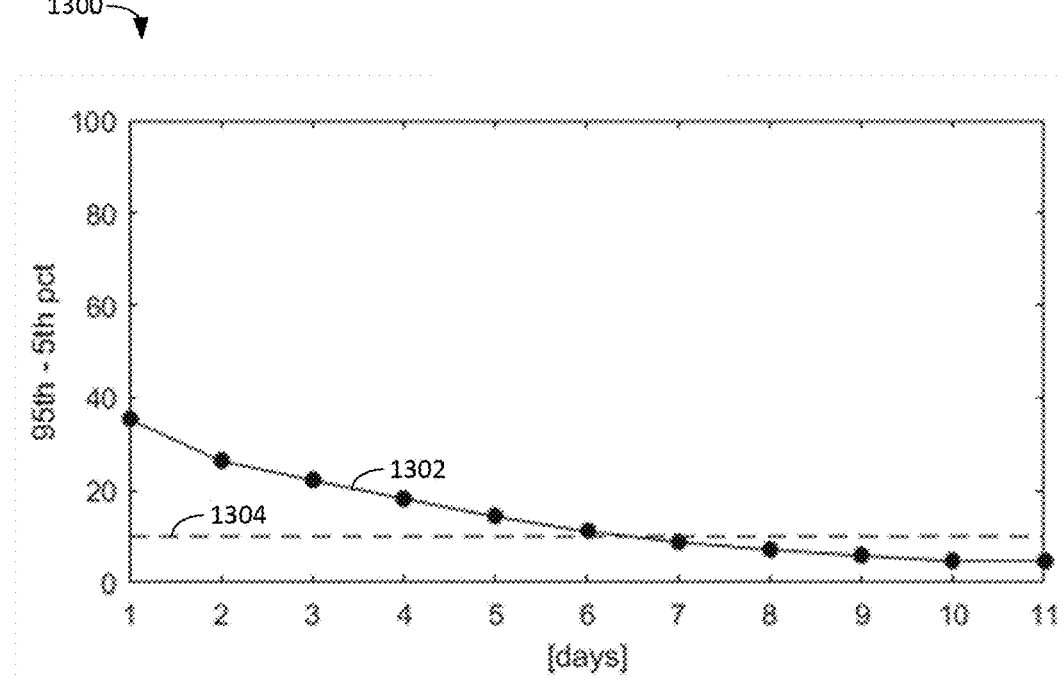
FIG. 13 illustrates a difference between the $5^{th}$ and $95^{th}$ percentile of the effect of the fifth calibration model parameter on the estimated blood glucose levels of the user as shown in FIG. 12.
Figure 14:
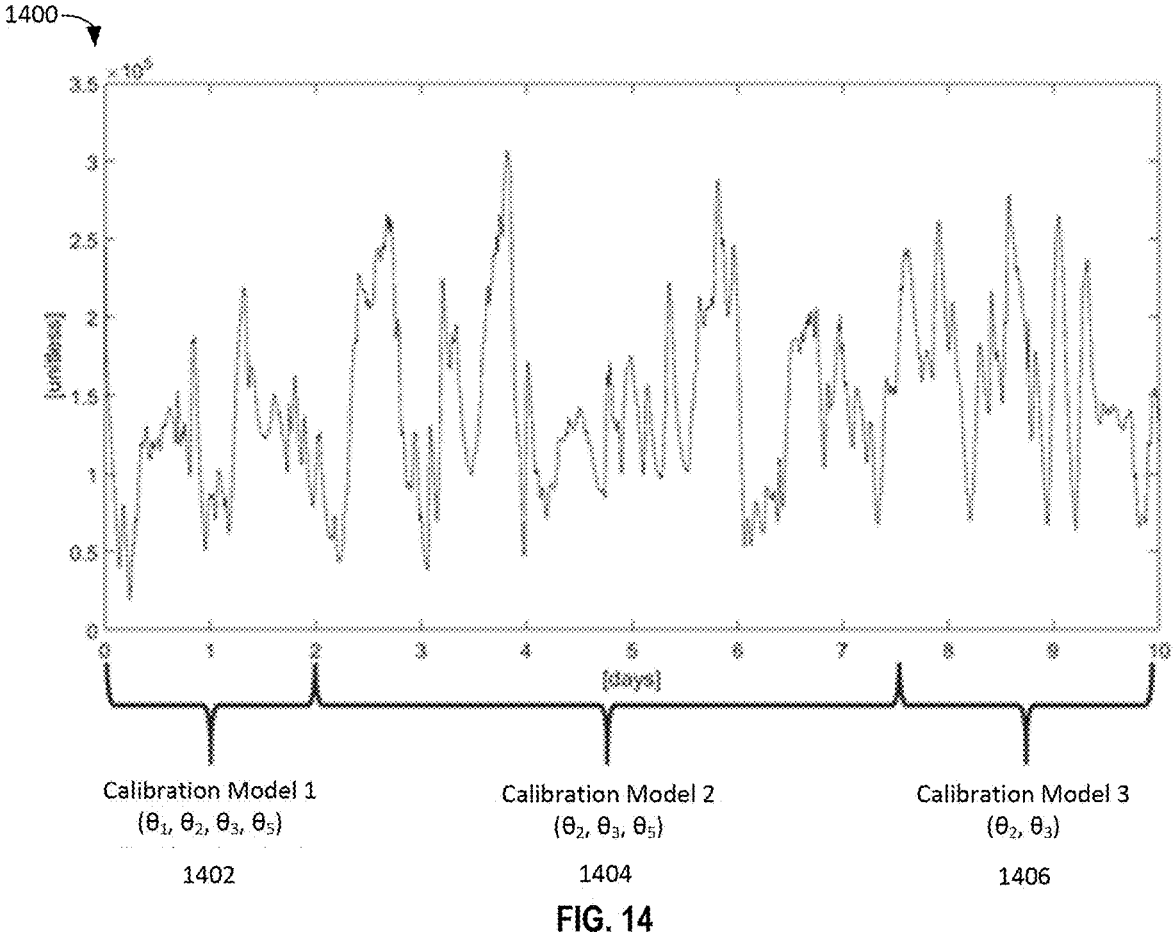
FIG. 14 illustrates a sample application of the calibration model parameters of FIGS. 6-13 to different temporal phases of a glucose monitoring session, in accordance with some embodiments.

FIG. 13 illustrates a difference 1302 between the $5^{th}$ and $95^{th}$ percentile 1205, 1202 of the effect of the calibration model parameter $\theta_5$ on the estimated blood glucose levels $u_f(t)$ of the user as shown in FIG. 12. A threshold 1304 of a 10 mg/dl difference in estimated blood glucose levels between the $5^{th}$ and $95^{th}$ percentile 1205, 1202 is shown, indicating a predetermined threshold below which the calibration model parameter $\theta_5$ may be determined not to have a substantial effect on the estimated blood glucose levels $u_f(t)$. However, the predetermined threshold of 10 mg/dl is exemplary and not limiting. Any predetermined threshold value may be utilized. Accordingly, this simulation indicates that the calibration model parameter $\theta_5$ has a substantial effect on the estimated blood glucose levels $u_f(t)$ during the first 6-7 days.

From the results of the global analysis, illustrated by FIGS. 6-13, FIG. 14 illustrates a sample application of the calibration model parameters $\theta_1$, $\theta_2$, $\theta_3$, $\theta_5$ of FIGS. 6-13 to different temporal phases 1402, 1404, 1406 of a glucose monitoring session, in accordance with some embodiments. As shown, the influence of baseline parameter $\theta_1$ on the calibration process may be restricted to a beginning phase 1402, e.g., the first two days of monitoring, while parameter $\theta_2$ is relevant for all phases 1402, 1404, 1406, e.g., the entire session. The influence of sensitivity parameter $\theta_3$ on the calibration process is relevant for all phases 1402, 1404, 1406, e.g., the entire monitoring session, while parameter $\theta_5$ only characterizes the beginning phase 1402 and the middle phase 1404, e.g., the first seven days, but not the end phase 1406, e.g., the last three days of the monitoring session. Therefore, the entire monitoring session may be characterized by different temporal phases, in which only the relevant calibration model parameters may be considered and estimated during the calibration process. Consequently, in some embodiments, the global calibration model would be defined by distinct candidate calibration models specific for each phase of the monitoring session, derived from the global calibration model of Eqs. 4 and 5 by considering only the meaningful calibration model parameters in each phase.

Figure 15:
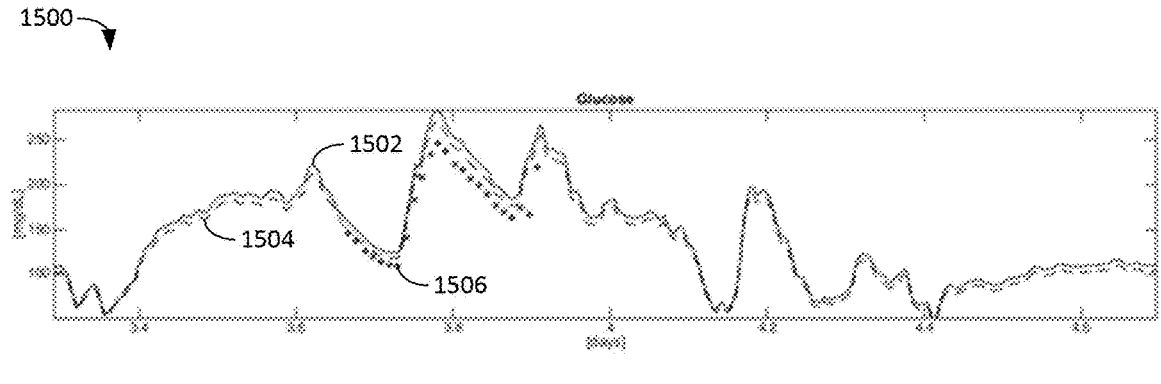
FIG. 15 illustrates a graphical relationship between blood glucose levels estimated by a global calibration model, blood glucose levels estimated by a model utilizing phase-specific calibration models, and actual self-measured blood glucose levels of a user, in accordance with some embodiments.

Calibrating the sensor signal $y_f(t)$ in each phase of the monitoring session utilizing candidate calibration models valid for each specific phase results in more accurate estimations of the blood glucose levels of a user, as illustrated by FIG. 15, which illustrates interstitial glucose levels 1504, estimated utilizing different calibration model parameters for different temporal phases of the monitoring session, as more accurately predicting blood glucose level references 1506 measured by SMBG, compared to interstitial glucose levels 1502 estimated utilizing a static calibration model, in accordance with some embodiments.

In some embodiments, the technique described above in connection with at least FIGS. 6-13 can be extended to further development. Indeed, the definition of different candidate calibration models may be based on time, as described above, but may also or alternatively be based at least in part on detecting patterns in the sensor signal $y_f(t)$ that correspond to a particular candidate calibration model, e.g., noise levels in the signal satisfying a threshold, dips or surges in the sensor signal $y_i(t)$ satisfying a predefined shape, duration, frequency, pattern, or threshold, and/or from any other information derived from the calibration model itself. For example, in some embodiments, a decrease in the average level of the sensor signal $y_i(t)$ over an interval of time satisfying a threshold may indicate that sensor sensitivity is declining and that a particular phase of the monitoring session has been or should be entered, for example the ending phase as previously described. As another example, in some embodiments, a dip in the sensor signal satisfying either a predetermined shape or satisfying a threshold dip amplitude may indicate that beginning phase characteristics are present and the beginning phase as previously described has been or should be entered. Such examples illustrate at least some ways in which determination of a phase of a monitoring session, and accordingly, selection of an appropriate calibration model may be made utilizing only the sensor signal $y_i(t)$ and not requiring periodic verification by SMBG reference samples from the user.

Other examples of metrics that can be used at least in part to determine the calibration model may be selected from the list including, but not limited to: the number of days the sensor has been in use (e.g., implanted); sensor sensitivity or whether there has been a decrease in signal sensitivity (e.g., change in amplitude and/or variability of the sensitivity of the sensor compared to one or more predetermined criteria), including magnitude and history; noise analysis (e.g., EOL noise factors (skewness, spikiness, & rotations)), duration, magnitude and history, spectral content analysis, pattern recognition); oxygen (e.g., concentration and/or whether there is a predetermined oxygen concentration pattern); glucose patterns (e.g., mean, variability, meal characteristics such as peak-to-peak excursion, expected vs. unexpected behavior such as after a meal if glucose is not rising as expected);

Selecting a Calibration Model from a Set of Candidate Calibration Models

The Bayesian approach suggests a probabilistic setup for model uncertainty, where different models are under consideration for a given phase of a monitoring session. In particular, let Y be the data provided by discrete data points of sensor signal $y_i(t)$ and $M=\{M_1, \ldots, M_K\}$ be a set of K candidate calibration models under consideration for calibrating Y within the given phase of the monitoring session. The probability density function of Y under the specific candidate calibration model $M_i$, where $i=1$, K is given by Eq. 20:

$$p(Y|\theta_i, M_i) \qquad \text{(Eq. 20)}$$

where $\theta_i$ is the vector of unknown parameters for the specific candidate calibration model $M_i$.

Eq. 20 may be interpreted as the probability that the data Y would result when the values of the parameters in $\theta_i$ are utilized in the candidate calibration model $M_i$. In order to evaluate Eq. 20, prior distributions for the probabilities of all of the parameters of each candidate calibration model $p(\theta_i/M_i)$ and for the models $p(M_i)$ themselves are introduced.

Selection of a calibration model may include determining the posterior probability (e.g., utilizing historical data) that each candidate calibration model $M_i$ under consideration would predict the data Y, utilizing Bayes' theorem given by Eq. 21:

$$p(M_i|Y) = \frac{p(Y|M_i)p(M_i)}{\sum_{i=1}^{K} p(Y|M_i)p(M_i)} \qquad \text{(Eq. 21)}$$

where $p(Y|M_i)$ may be interpreted as the probability that data Y would occur from utilizing candidate calibration model $M_i$, where $p(M_i)$ may be interpreted as the probability of candidate calibration model $M_i$ being utilized, and where $$\sum_{i=1}^{K} p(Y|M_i)p(M_i)$$

may be interpreted as the sum of the probability that data Y would occur from utilizing candidate calibration model $M_i$ multiplied by the probability of candidate calibration model $M_i$ being utilized, for each of the K candidate calibration models.

$p(Y|M_i)$ given in the numerator of Eq. 21 may be further described by Eq. 22:

$$p(Y|M_i) = \int p(Y|M_i, \theta_i)p(\theta_i|M_i)d\theta_i \qquad \text{(Eq. 22)}$$

where the right side of Eq. 22 describes the integrated likelihood of $M_i$ and may be interpreted as the integral performed across a range of unknown parameters in the vector $\theta_i$ of the probability that data Y would occur from utilizing candidate calibration model $M_i$ utilizing the particular value of unknown parameters vector $\theta_i$ multiplied by the probability of the particular value of unknown parameters vector $\theta_i$ being utilized for candidate calibration model $M_i$.

Eq. 22 may be computed by different numerical integration strategies, for example utilizing Monte Carlo simulation methods.

Assume, for example, given a monitoring session of 10 days, that we can identify three generic sensor phases: a beginning phase (approximatively the first 2 days), an ending phase (approximatively the last 2-3 days) and a middle phase (between the beginning and ending phases). The phases may then be termed $M_{beg}$, $M_{mid}$, and $M_{end}$. Each sensor session may be characterized by its specific set of K candidate calibration models, $M_i=\{M_1, M_2, \ldots, M_K\}$.

For example, within beginning phase $M_{beg}$, $M^+$ indicates a model utilizing a beginning-session component, e.g., a signal artifact, as previously described, for the generic model M. Thus, considering all K candidate models, at the beginning of the session it is desirable to account for the possible presence of these components. Thus, the set of candidate calibration models for the beginning of the session becomes $$M_{beg} = \{M_1^+, M_1, \ldots, M_K^+, M_K\},$$

where for each of the K models we account for both the possible presence and the possible absence of beginning-phase components/artifacts. In an analogous way, in some embodiments, the same K candidate models $M_{mid}=\{M_1, M_2, \ldots, M_K\}$ may describe the middle phase. The last days of the monitoring session may be characterized by specific time-varying components, e.g., signal loss of sensitivity, as previously described. With ending phase $M_{end}$, $M^*$ indicates a model utilizing an end-of-session component. Thus, the set of candidate calibration models for the end of the session becomes $$M_{end} = \{M_1^*, M_1, \ldots, M_K^*, M_K\},$$

where for each of the K models we account for both the possible presence and the possible absence of end-phase components/artifacts.

In a real-time calibration scenario, given a set of data measures Y (which may be derived from SMBG measurements and/or from auto-calibration processes), evaluation of a posteriori model probability is performed for each candidate calibration model for the specific time-phase during which the calibration occurs, utilizing Eq. 21, and the candidate calibration model having the highest probability is selected.

Implementing such a process requires: 1) the specification of all a priori probability distributions for each model and each model's unknown parameters; and 2) the computation of the integrated likelihood $p(Y|M_i)$ as described in Eq. 22. Strategies for both are presented in the following paragraphs.

Specifying a Priori Probabilities for Candidate Calibration Model Selection

Both a priori models probabilities for both the models themselves and for the unknown model parameters of each model are needed for selecting a particular candidate calibration model. Such a priori probabilities may be provided by deriving average distributions on real-data in a cross-validation scenario. For instance, the probability of each model being utilized in a particular population may be derived by off-line fitting of all candidate calibration models on real datasets previously recorded from monitoring sessions of the same or different users. For example, server 250 of FIG. 2, having memory 258 and processor(s) 256, may be configured to perform such off-line fitting and communicate a result to monitor 220 via transceiver 254 and transceiver 224. For each sensor type, the candidate calibration model that best fits the data may be selected and the probability of utilizing a specific calibration model in the population may be averaged from that results. As previously described, in some embodiments, the probability of a specific candidate model may also be modified in real-time by examining the sensor signal. Indeed, specific signal patterns that are strictly related to a specific model candidate may be detected in real-time thereby increasing the probability of utilizing the corresponding candidate calibration model. Such real-time examination may be performed, for example, by server 250 of FIG. 2 after communicating the sensor data from monitor 220 to server 250 via transceivers 254, 224, or alternatively by monitor 220 itself.

Similarly, a priori probabilities for the unknown model parameters may be derived from real data by off-line identification, for example, by server 250 of FIG. 2. Given the probabilistic framework for calibration, it is important to consider correlations between all model parameters. Indeed, different candidate models may have similar mean values for their parameters, but different correlations between parameters. Accordingly, independence between parameters is not assumed. Instead, all parameters correlations may be estimated from real data. Specifically, given a training size of N samples, let $\theta$ be the vector of estimated parameters for the generic model M. Parameters vector $\theta$ is assumed to be distributed with prior mean $\mu_\theta$ and prior covariance matrix $\Sigma_\theta$, where the $i^{th}$ element $\mu_i$ of $\mu_\theta$, and the $ij^{th}$ element $\sigma_{ij}$ of $\Sigma_\theta$, are defined as averages taken across the N samples according to Eqs. 23 and 24, respectively:

$$\mu_i = \frac{1}{N} \sum_{n=1}^{N} \theta_{n,i} \tag{Eq. 23}$$

$$\sigma_{ij} = \frac{1}{N-1} \sum_{n=1}^{N} (\theta_{n,i} - \mu_i)(\theta_{n,j} - \mu_j) \tag{Eq. 24}$$

Computing the Integrated Likelihood of the Candidate Calibration Models for Model Selection In some cases, the integral of Eq. 22 may be evaluated analytically, while in others it may be computed by numerical approximation methods. Several approximation techniques, such as asymptotic approximation through Laplace's method, Monte Carlo integration, variance reduction techniques such as importance sampling, Gaussian quadrature and Markov chain Monte Carlo methods are contemplated. However the present application is not so limited and any appropriate approximation technique may be utilized.

In some embodiments, the use of Monte Carlo techniques may be particularly suitable for this specific application. The simple Monte Carlo integration approximates the marginal likelihood that data Y would be accurately predicted by calibration model $M_i$ by averaging the likelihood values over a set of $N_{iter}$ iterations, as shown by Eq. 25:

$$\hat{p}(Y|M_i) = \frac{1}{N_{iter}} \sum_{n=1}^{N_{iter}} p(Y|M_i, \theta_n) \tag{Eq. 25}$$

where at each iteration n a set of model parameters $\theta_n$ is sampled from the prior distribution of offline samples, as described above, and the probability of the observed data Y, given the specific set of parameters $\theta_n$, is computed, for example by server 250 of FIG. 2 and communicated to monitor 220 via transceivers 254, 224.

Accordingly, the integrated likelihood of Eq. 22 may be approximated by averaging over the $N_{iter}$ iterations:

$$\int p(Y|M_i, \theta_i) p(\theta_i|M_i) d\theta_i = \tag{Eq. 26}$$

$$E[p(Y|M_i, \theta_i)] \sim \frac{1}{N_{iter}} \sum_{n=1}^{N_{iter}} p(Y|M_i, \theta_n)$$

where $E[p(Y|M_i\theta_i)]$ is the expected value of the integrated likelihood of Eq. 22, the average of the likelihoods of the sampled parameters values ($\{\theta_n: n=1, \ldots, N_{iter}\}$).

In some circumstances, a majority of the sampled parameters values $\theta_n$ may have small likelihood values, requiring a large number of iterations to reach convergence. In such circumstances, the precision of the simple Monte Carlo integration may be improved by the use of variance reduction techniques such as importance sampling.

Estimating Unknown Model Parameters for the Selected Calibration Model

Once a calibration model M is selected as having the highest a posteriori probability for accurately calibrating the sensor signal, the correspondent vector of model parameters $\theta$ may be estimated so that actual calibration using calibration model M can be carried out.

Each time a new SMBG is acquired for calibration at time $t_i$, $i=1, 2, \ldots, S$ (where S represents the total number of BG samples used for calibration), the set of parameters θ may be updated to exploit each new measure $u_B(t_i)$ and, in some embodiments, all previously acquired BG samples. In particular, a relation between the BG reference samples $u_B$ and estimated blood glucose values $\hat{u}_B(\theta)$, obtained by transforming the current samples contained in vector $y_I$ utilizing the selected calibration model M and the calibration model parameters in the vector θ, may be expressed in vector form as shown in Eq. 27:

$$u_B = \hat{u}_B(\theta) + e \qquad \text{(Eq. 27)}$$

where $u_B$ is the i×1 vector containing the SMBG samples acquired at calibration times $t_j$, j=1, . . . , i (i=1, . . . , S), $u_B=[u_B(t_1), \ldots, u_B(t_{i-1}), u_B(t_i)]^T$, $\hat{u}_B(\theta)$ is the i×1 vector obtained transforming the estimated blood glucose values of the i×1 vector $y_I$, containing $y_I(t_j)$, j=1, . . . , I, into BG values utilizing the selected calibration model M and the calibration model parameters in the vector θ, and i×1 vector e represents the error between $u_B$ and $\hat{u}_B(\theta)$.

In some embodiments, error vector e is assumed to contain white noise samples, uncorrelated with θ, having zero mean, and covariance matrix $\Sigma_e$. The error variance is assumed constant over time and its value is estimated from an off-line training set of previously calibrations for the same or another user. Note that the length i of the vectors in Eq. 27 increases by one unit each time a new SMBG is acquired for calibration, since in some embodiments, all previous measures are considered.

The correspondent vector of model parameters θ may be estimated utilizing Eq. 28:

$$\hat{\theta} = \underset{\theta}{\text{argmin}}\left\{[u_B - \hat{u}_B(\theta)]^T \Sigma_e^{-1}[u_B - \hat{u}_B(\theta)] + (\mu_\theta - \theta)^T \Sigma_p^{-1}(\mu_\theta - \theta)\right\} \qquad \text{(Eq. 28)}$$

where $\hat{\theta}$ is the vector of estimated model parameters, $$\underset{\theta}{\text{argmin}}$$

indicates that values of the vector $\hat{\theta}$ that results in a minimum of the function in brackets are sought, $u_B$ is the vector containing SMBG reference samples acquired via, for example finger prick, for calibration, $\hat{u}_B(\theta)$ is the vector of the estimated blood glucose values obtained by transforming the current samples contained in vector $y_I$ utilizing the selected calibration model M and the calibration model parameters in the vector θ, the matrix $\Sigma_e$ represents the covariance of the error between SMBG reference samples and actual blood glucose levels, and where the unknown parameters vector θ is estimated exploiting the data contained in $u_B$ and $y_I$ in addition to some a priori knowledge on the distribution of θ, described by the mean $\mu_\theta$ and the covariance matrix $\Sigma_\theta$, which may be determined utilizing Eqs. 23 and 24.

Figure 16:
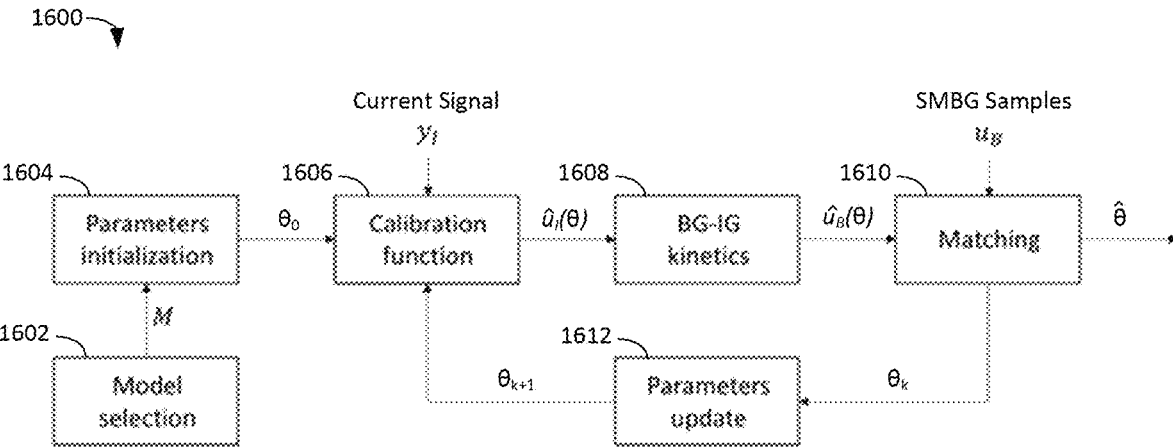
FIG. 16 illustrates a flowchart for estimating unknown calibration model parameters, in accordance with some embodiments.

Since no closed form solution exists for the minimization problem of Eq. 28, the estimate $\hat{\theta}$ is found by iteratively stepping through each parameter possible value of the parameter vector θ, schematically summarized by the flowchart 1600 of FIG. 16. In some embodiments, the procedure described by flowchart 1600 may be performed by server 250 or by monitor 220 of FIG. 2, for example, specifically by processor(s) 256 and memory 258, or processor(s) 226 and memory 228, respectively. Moreover, such a method is not limited to the specific steps described in flowchart 1600 and may omit one or more of the below-described steps and/or include one or more additional steps not described in flowchart 1600 but described elsewhere in this application.

At block 1602, model M is selected as having the highest a posteriori probability of fitting the data, as previously described. For example, processor(s) 256 of server 250, or processor(s) 226 of monitor 220 in FIG. 2 may perform the selection as previously described. Flowchart 1600 advances from block 1602 to block 1604.

At block 1604, a parameters vector θ is initialized or set to an initial value, e.g., its prior mean value, $\theta_0=\mu_\theta$. For example, processor(s) 256 of server 250, or processor(s) 226 of monitor 220 in FIG. 2 may perform the initialization of parameters vector θ to $\theta_0=\mu_\theta$ in memory 258 or memory 228, respectively. Flowchart 1600 advances from block 1604 to block 1606 with parameters vector θ set to $\theta_0=\mu_\theta$.

At block 1606, sensor signal $y_I$ may be received and utilized to estimate the IG profile $\hat{u}_I(\theta)$ according to the selected calibration model M using the parameters vector θ set to initial values $\theta_0=\mu_\theta$, as previously described in Eqs. 5 and 15. For example, processor(s) 256 of server 250, utilizing memory 258, or processor(s) 226 of monitor 220, utilizing memory 228, in FIG. 2 may transform the sensor signal $y_I$ into the estimated interstitial glucose level $\hat{u}_I(\theta)$ of the user utilizing the selected calibration model M and the initial value of the one or more calibration model parameters $\theta_0$. Flowchart 1600 advances from block 1606 to block 1608.

At block 1608, BG profile, $\hat{u}_B(\theta)$ may be estimated from the estimated IG profile $\hat{u}(\theta)$, by means of deconvolution, utilizing for example a non-stochastic approach, as previously described in connection with FIG. 3 and Eqs. 1-5, thereby accounting for the distortion introduced by the BG-IG kinetics. For example, processor(s) 256 of server 250, utilizing memory 258, or processor(s) 226 of monitor 220, utilizing memory 228, in FIG. 2 may estimate the blood glucose level $\hat{u}_B(\theta)$ based on the estimated interstitial glucose level $\hat{u}_I(\theta)$ by deconvolution.

For computational reasons, the deconvolution may be applied to temporal windows containing the time instant $t_j$, j=1, . . . , I at which each SMBG is acquired. Practically, for each of the i SMBG measures collected in vector $u_B$, a time window Λ from $t_j$−100 min to $t_j$+5 min may be considered, although any other appropriate time window may also be utilized. Letting $u_{I(\Lambda)}$ be the n×1 vector containing the IG estimations of the previous step at the sampling instants lying within Λ, a uniform sampling grid, with, e.g., 5-min steps, may be defined: $\Omega_s=\{t_1, t_2, \ldots, t_n\}$. In addition, w is defined as the n×1 vector of measurement error w(t) at time instants in $\Omega_s$, assumed to have zero mean and covariance matrix $\Sigma_w=\sigma^2 R$, with $\sigma^2$ unknown constant and R n×n known matrix whose structure reflects expectations on measurement error variance. Here, $R=I_n$ current signal with variance constant over time. The vector $u_{B(\Lambda)}$ is defined as the N×1 unknown vector containing samples of $u_B(t)$ at time instants on a virtual grid $\delta_v=\{t_{v1}, t_{v2}, \ldots, t_{vN}\}$, which is independent of and usually denser than $\Omega_s$. Here an exemplary, non-limiting, uniform 1-min step may be used. In order to allow initial condition transients to vanish, $\Omega_v$ starts from $t_1$−100 min, so that the reconstruction of $u_B(t)$ is not altered in the window of interest A.

Once all variables have been defined, having $\Omega_s$ and $\Omega_v$ both uniform, with $\Omega_s \subseteq \Omega_v$, the following matrix equation may be written as shown in Eq. 29:

$$u_{I(\Lambda)} = H \cdot u_{B(\Lambda)} + w \qquad \text{(Eq. 29)}$$

where H is the n×N matrix obtained by downsampling the N×N transfer matrix $H_v$ of the BG-IG system, maintaining only the rows correspondent to sampling instants in $\Omega_s$.

According to the fact that vector $u_{B(\Lambda)}$ contains samples of a BG profile, which is a biological signal expected to have a certain smoothness, a double integrated white noise model of unknown variance $\lambda^2$ may be chosen to describe entries of $u_{B(\Lambda)}$. Thus, the covariance matrix of $u_{B(\Lambda)}$ may be expressed as Eq. 30:

$$\sum\nolimits_{u_{B(\Lambda)}} = \lambda^2 \left(F^T F\right)^{-1} \qquad \text{(Eq. 30)}$$

where F may be defined as a N×N Toeplitz lower-triangular matrix having $[1, -2, 1, 0, \ldots, 0]^T$ as a first column.

Assuming that $u_{B(\Lambda)}$ and w are uncorrelated, the following quadratic optimization problem of Eq. 31 corresponds to the linear minimum error variance Bayesian estimate of $u_{B(\Lambda)}$:

$$\hat{u}_{B(\Lambda)} = \qquad \text{(Eq. 31)}$$

$$\underset{\hat{u}_{B(\Lambda)}}{\operatorname{argmin}} \left\{ (u_{I(\Lambda)} - Hu_{B(\Lambda)})^T R^{-1} (u_{I(\Lambda)} - Hu_{B(\Lambda)}) + \gamma u_{B(\Lambda)}^T F^T F u_{B(\Lambda)} \right\}$$

where parameter $$\gamma = \frac{\sigma^2}{\lambda^2},$$

estimated by Maximum Likelihood, represents the regularization term that balances the data fit with the smoothness of the estimated profile.

The optimization problem of Eq. 31 has a closed form solution, which may be expressed as Eq. 32:

$$\hat{u}_{B(\Lambda)} = \left(H^T R^{-1} H + \gamma F^T F\right)^{-1} H^T R^{-1} u_{I(\Lambda)} \qquad \text{(Eq. 32)}$$

For every SMBG measurement in vector $u_B$, the BG profile $\hat{u}_{B(\Lambda)}$, which depends on parameter vector $\theta_k$, may be estimated inside the window $\Lambda$ that contains the time instant at which the SMBG sample $t_j$, j=1, . . . , i is acquired.

Flowchart 1600 may then advance from block 1608 to block 1610, where an error (e.g., a difference) may be determined between the estimated BG profile $\hat{u}_B(\theta)$ and actual SMBG samples $u_B$, measured via finger prick or any other means of blood glucose reference determination. For example, processor(s) 256 of server 250, utilizing memory 258, or processor(s) 226 of monitor 220, utilizing memory 228, in FIG. 2 may determine this error.

For example, for each SMBG sample in vector $u_B$, acquired at time $t_j$, j=1, . . . , i, the correspondent estimated value of $\hat{u}_{B(\Lambda)}$ at time $t_j$ is considered, composing the vector $\hat{u}_B(\theta_k)$ used in Eq. 28, as given by Eq. 33:

$$\hat{u}_B(\theta_k) = [\hat{u}_B(t_1, \theta_k), \ldots, \hat{u}_B(t_{i-1}, \theta_k), \hat{u}_B(t_i, \theta_k)]^T \qquad \text{(Eq. 33)}$$

Flowchart 1600 may then advance from block 1610 to block 1612, where the parameters vector $\theta$ may be updated for the following iteration (from $\theta_k$ to $\theta_{k+1}$). For example, at each iteration k, the parameters vector $\theta_k$ may be updated to a new set of values, $\theta_{k+1}$, using the Nelder-Mead simplex algorithm, for example. In some embodiments, processor(s) 256 of server 250, utilizing memory 258, or processor(s) 226 of monitor 220, utilizing memory 228, in FIG. 2 may update the one or more calibration model parameters $\theta$ based on the difference between the estimated blood glucose level and a reference of the blood glucose level of the user.

Blocks 1606, 1608, 1610 and 1612 may be reiterated until one of the following stopping criteria occurs: 1) the step size in parameters update is smaller than a fixed tolerance (e.g. $10^{-6}$); 2) the relative change in the value of the objective function is lower than a fixed tolerance (e.g. $10^{-6}$). In some embodiments, processor(s) 256 of server 250, utilizing memory 258, or processor(s) 226 of monitor 220, utilizing memory 228, in FIG. 2 may recursively re-estimate the interstitial glucose level $\hat{u}_I(\theta)$ and the blood glucose level $\hat{u}_B(\theta)$ based on the selected calibration model and the one or more updated calibration model parameters $\theta$ until a predefined relationship between the reference of the blood glucose level of the user and at least one of the estimated interstitial glucose level and the estimated blood glucose level is present. For example, such a predefined relationship may include but is not limited to at least one of the estimated interstitial glucose level and the estimated blood glucose level being within a predetermined accuracy of the reference of the blood glucose level of the user.

For each of the S SMBG samples used for calibration, once calibration model parameters vector $\hat{\theta}$ has been estimated as described in connection with FIG. 16, the parameters vector $\hat{\theta}$ may be used to calibrate, in real-time, the current signal $y_I(t)$ utilizing Eq. 15.

In particular, being the SMBG samples acquired at times $t_i$, i=1, 2, . . . , 5, the parameters estimated at the $i^{th}$ calibration may be used to calibrate the sensor signal $y_I(t)$ from $t_i$+five min to $t_{i+1}$+five min, or any other appropriate timing offset from contiguous time instants. Indeed, the deconvolution window $\Lambda$ is defined to end five min, or any other appropriate timing offset, after the reference time of the BG measurement in order to avoid edge effects.

Some Embodiments of a Method for Monitoring a Blood Glucose Level of a User

Several embodiments of methods for monitoring blood glucose levels of a user are described in this application. FIG. 17 illustrates an exemplary flowchart 1700 of a method for monitoring a blood glucose level of a user, in accordance with some embodiments. One or more of the steps presented in flowchart 1700 may be performed by processor(s) 256 of server 250, utilizing memory 258, or processor(s) 226 of monitor 220, utilizing memory 228, as previously described in connection with FIG. 2. Moreover, such a method for monitoring a blood glucose level of a user is not limited to the specific steps described in flowchart 1700 and may omit one or more of the below-described steps and/or include one or more additional steps not described in flowchart 1700 but described elsewhere herein.

Flowchart 1700 includes block 1702, which includes receiving a time-varying electrical signal from an analyte sensor during a temporal phase of a monitoring session. For example, as previously described, processor(s) 256 of server 250 or processor(s) 226 of monitor 220 may be configured to receive the sensor signal $y_f(t)$ from sensor 202 of sensor assembly 210, as shown in FIG. 2.

In some embodiments, a reference input may be received. For example, as previously described, processor(s) 256 of server 250 or processor(s) 226 of monitor 220, as shown in FIG. 2, may be configured to receive a reference input. The reference input may include any of a blood glucose reference, a noise metric of the time-varying electrical signal, an impedance of the analyte sensor 202, an input from a sensor 205 configured to measure at least one of an acceleration of the user, a galvanic response, an impedance of the sensor and/or tissue, a second electrochemical sensor, a temperature and an atmospheric pressure.

Flowchart 1700 may advance from block 1702 to block 1704, which includes selecting a calibration model from a plurality of calibration models, wherein the selected calibration model comprises one or more calibration model parameters. For example, as previously described, processor(s) 256 of server 250 or processor(s) 226 of monitor 220, as shown in FIG. 2, may be configured to select a calibration model M from a plurality of calibration models $M_f \ldots M_k$ as previously described. The selected calibration model M includes one or more calibration model parameters $\theta$.

Flowchart 1700 may advance from block 1704 to block 1706, which includes estimating at least one of the one or more calibration model parameters of the selected calibration model based on at least the time-varying electrical signal during the temporal phase of the monitoring session. For example, processor(s) 256 of server 250 or processor(s) 226 of monitor 220, as shown in FIG. 2, may be configured to estimate at least one of the one or more calibration model parameters $\theta$ of the selected calibration model M based on at least the time-varying electrical signal $y_f(t)$ during the temporal phase of the monitoring session.

Flowchart 1700 may advance from block 1706 to block 1708, which includes estimating the blood glucose level of the user based on the selected calibration model and using the at least one estimated parameter. For example, processor(s) 256 of server 250 or processor(s) 226 of monitor 220, as shown in FIG. 2, may be configured to estimate the blood glucose level $\hat{u}_B(\theta)$ of the user based on the selected calibration model M and using the at least one estimated parameter $\theta$.

Assessing the Accuracy of Methods, Utilizing Simulated Data

Figure 18:
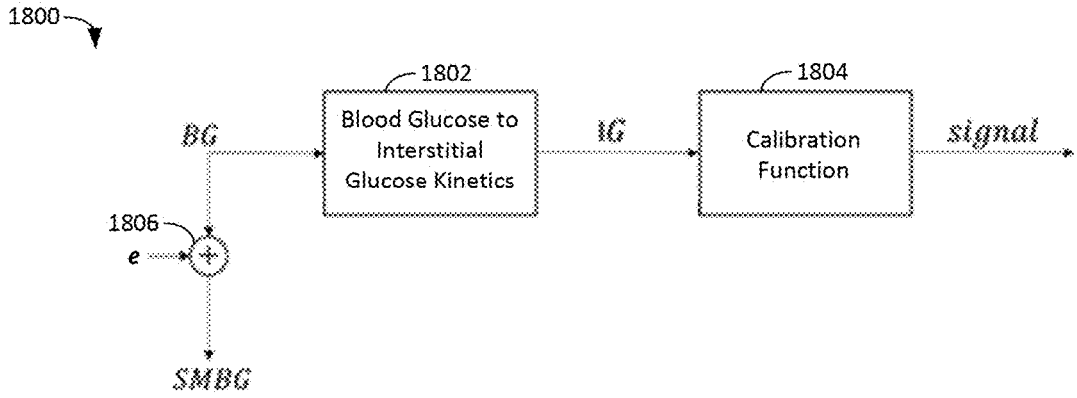
FIG. 18 illustrates a flowchart for verifying calibration models via simulating blood glucose, interstitial glucose (IG), self-measured blood glucose, and sensor signal values, in accordance with some embodiments.

The accuracy of the mixture model Bayesian calibration approach described above may be assessed using an example simulation graphically described by FIG. 18, which illustrates a schematic diagram 1800 for simulating blood glucose, interstitial glucose, self-measured blood glucose, and sensor signal values for verifying calibration models, in accordance with some embodiments. As shown, a blood glucose (BG) trace is simulated using a UVA/Padova type 1 diabetes simulator. From the BG trace, random SMBG measures (approximatively one every 24 h) are simulated by adding noise e according to the model described by Eq. 27, where $$e \sim N(0, \sigma_e^2),$$

$$\sigma_e^2$$

is the covariance of the error e, twenty in this example, and the mean of the error e is zero.

The interstitial glucose (IG) trace may be obtained from the BG profile accounting for the BG-to-IG kinetics by means of convolution according to Eq. 3, where the parameter r is sampled from its prior distribution $$(\tau \sim N(\mu_\tau, \sigma_\tau^2)),$$

in some embodiments assumed to be a lognormal distribution, here $\mu_\tau = 7.5$ and $$\sigma_\tau^2 = 2.25$$

are assumed.

Figure 19:
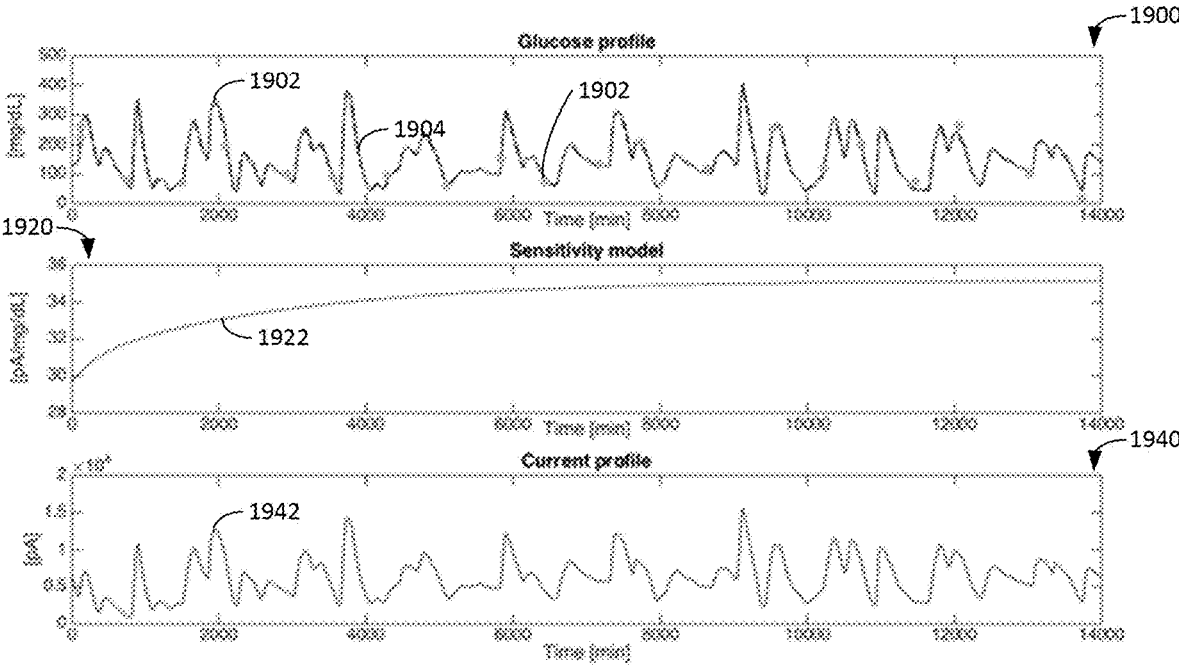
FIG. 19 illustrates results of the simulated values of FIG. 18, in accordance with some embodiments.

An example of the simulated IG profile 1902 (solid line), BG profile 1904 (dotted line) and SMBG measurements 1906, indicated by dots, are shown in first panel 1900 of FIG. 19.

The calibration model is chosen among the following set M of three example candidate calibration models: $M = \{M_1, M_2 \ldots M_i\}$, where $i=3$. In particular, the structure of the set M of candidate models is given by Eq. 5 with b(t) defined by Eq. 6, and $s_i(t)$, $i=1, 2, 3$ specified by Eqs. 7-9, for $i=1, 2, 3$ respectively.

In this specific simplified example, the three candidate models differ for the definition of the sensitivity functions $s_i(t)$. Indeed, sensitivity $s_1(t)$ of model $M_1$, of Eq. 7 is described by a bi-exponential function, sensitivity $s_2(t)$ of model $M_2$ of Eq. 8 is described by a mono-exponential function, and sensitivity $s_3(t)$ of model $M_3$ of Eq. 9 is described by a linear function. Note that, in this simulation setup, no beginning-phase and end-phase components are considered, rather a single phase of the monitoring session is described for simplicity only.

Each of the three models has a priori probability specified by $p(M_i)$, $i=1, 2, 3$. Specifically, $p(M_1)=0.5$, $p(M_2)=0.25$, $p(M_3)=0.25$. According to these probabilities, one of the three models is sampled from the discrete distribution $p(M)$. The simulated sensor signal is obtained from the IG profile by using the specific model structure given by Eqs. 5 and 6 as well as the respective one of Eqs. 7-9, depending on the selected model. FIG. 19 depicts an example of simulated sensitivity profile $s_1(t)$ 1922, obtained with model $M_1$, in second panel 1920 of FIG. 19, and the corresponding simulated sensor signal $y_f(t)$ 1942 in third panel 1940 of FIG. 19.

Once the sensor signal $y_f(t)$ is simulated we apply the new mixture model Bayesian calibration approach for model selection. The selected model may then be compared with the model that actually generated the data (e.g., $M_1$ in this example) to assess the efficacy of this method.

In order to find the model that actually generated the data (e.g., $M_1$ in this example), following the Bayesian approach we need to evaluate the probability of each model given the set of data just generated above and chose the model that maximizes this probability. Formally, for each of the three models, evaluation under Eq. 21 where Y, in this specific case, is the simulated set of SMBGs.

As can be seen in Eq. 21, the denominator does not depend on the specific model. Thus, to compare the different a posteriori probabilities only the numerators need be compared for all the three models. As stated above, the prior probabilities are $p(M_1)=0.5$, $p(M_2)=0.25$, $p(M_3)=0.25$ and the model likelihoods given by Eq. 22 are computed by simple Monte Carlo integration as per Eq. 25 with, e.g., $10^8$ iterations per model. The result of the Monte Carlo simulation indicate $M_1$ as the most probable model a priori, which was the model utilized to generate the data for the simulation. Thus, the present concepts are validated as an accurate method for selecting calibration models that most accurately estimate blood glucose levels of a user.

Assessing the Accuracy of Methods, Utilizing Real Data

To assess the above-described method(s) on real data, a priori probabilities for each parameter of each candidate model must be derived. Moreover, the assessment may be carried out in a situation where different models would arrive at substantially different estimations of blood glucose levels. For example, testing the above-described method(s) at the end of a sensor session may be beneficial since different sensitivity models may capture a possible loss of sensitivity of the sensor.

One simplified, non-limiting scenario would be a two-candidate calibration model having a stable sensitivity model $M_s$ and a model factoring in a loss of sensitivity $M_l$. For such a scenario, a set M of candidate calibration models may have the form: $M=\{M_s, M_l\}$ and may utilize a set of previously received and/or archived SMBG samples from one or more users as data Y. For such a model, sensitivity profiles for the stable sensitivity and for the loss of sensitivity models may be given by Eqs. 34 and 35, respectively.

$$s_s(t) = m_0 \cdot \left\{ 1 + \frac{m_f - m_0}{m_0} \cdot [driftCurve(t)] \right\} \quad \text{(Eq. 34)}$$

$$s_l(t) = m_0 \cdot \left\{ 1 + \frac{m_f - m_0}{m_0} \cdot [driftCurve(t)] \right\} + [a \cdot t + b] \quad \text{(Eq. 35)}$$

where driftCurve(t) is a function modeling a drift in the sensor sensitivity not accounting for as a loss of sensitivity of the sensor and $[a \cdot t + b]$ is a term accounting for a loss of sensitivity of the sensor, where the model $M_l$ is utilized after time $T_{switch}=-b/a$.

A sub-population of SMBGs may be determined offline for each sensitivity model based on a fit with one or the other of $s_s(t)$ and $s_l(t)$ and each sub-population of SMBGs may be utilized to derive a priori distributions for each model itself and for all model parameters of each model.

Figure 20:
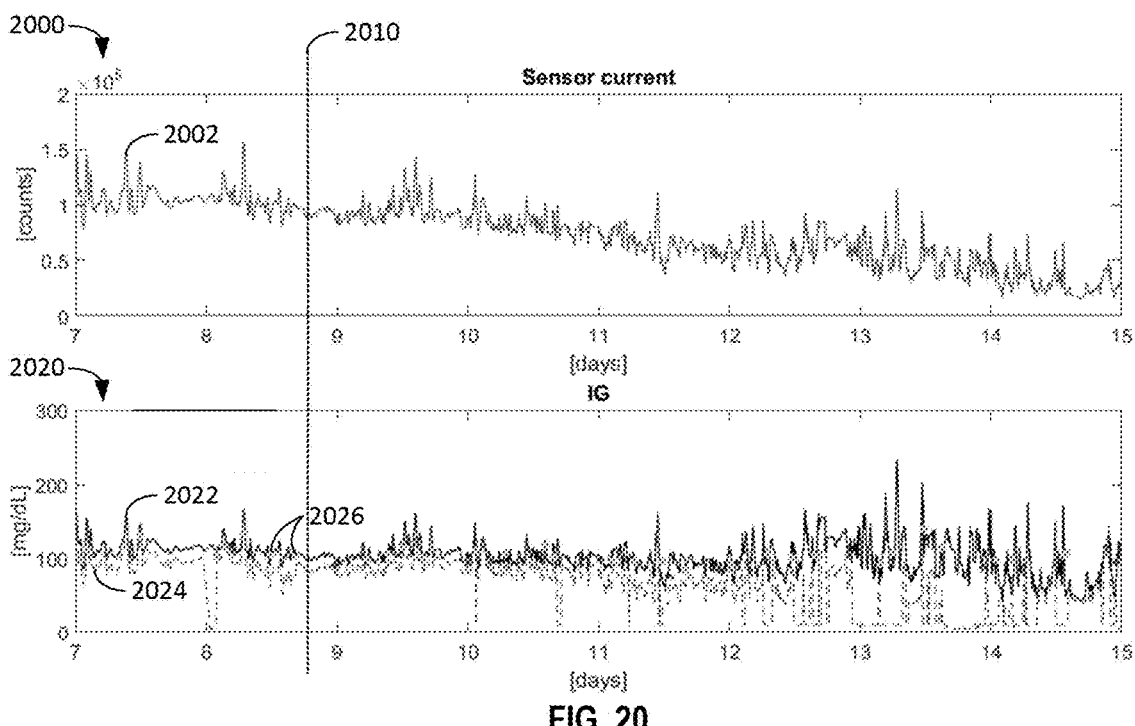
FIG. 20 illustrates relationships between a sensor signal and IG levels estimated via global calibration model, phase-specific calibration models, and self-measured blood glucose levels, in accordance with some embodiments.

FIG. 20 illustrates a first plot 2000 including a sensor signal 2002 and a second plot 2020 including a IG level 2022 estimated by a global calibration model, a IG level 2024 estimated by $M_s$ before time $T_{switch}$ 2010 and $M_l$ thereafter, and SMBG references 2026 (dots). Estimated IG level 2022 becomes increasingly inaccurate, compared to SMBG references 2026 after time $T_{switch}$ 2010. However, estimated IG level 2024 is much more accurate, tracking much more closely with SMBG references 2026, especially after time $T_{switch}$ 2010. Accordingly, a calibration model which switches from a stable sensitivity model to a sensitivity loss model based on time and utilizing SMBGs is validated.

As previously described, assessment utilizing SMBG and other signal-based metrics may be utilized to further increase the accuracy of the calibration model. Non-limiting examples of such signal-based metrics may include identification of a downward drift metric, a noise duration metric and a physiologic noise metric, each of which may indicate that a transition to a different candidate calibration model (e.g., from stable model $M_s$ to loss model $M_l$) may yield a more accurate glucose estimation. In some embodiments, if the likelihood of the presence of any one or combination of these signal-based metrics in the sensor signal exceeds a threshold (e.g., 0.5), a selection of and switch to the loss model may be validated. Further including the utilization of signal-based metrics in the selection of a calibration model may allow an accurate selection some time in advance of when an accurate selection would otherwise be made utilizing SMBG samples alone.

One example of a downward drift metric may be determined based in part on a slow moving average of raw sensor data (e.g., counts). This embodiment takes advantage of the fact that for most patients, the average glucose over time (e.g., a few days or more) remain relatively constant; thus, a change in the average of the sensor data (e.g., uncalibrated (raw or filtered) over time (e.g., 2, 3, 4, 5, 6, 7 days or more) may be interpreted as a change sensitivity of the sensor over time. The results of the slow-moving average could be a quantifiable amount and/or simple yes/no indicators of a sensitivity decline that may be useful as one input or variable into the end-of-life function. For example, the processor module may use an average of the last x hours (e.g. for 24 hours), a rectangular window averaging or an alpha filter with an exponential forgetting factor to compute the slow-moving average to evaluate sensor sensitivity over time. In one example of an alpha filter with exponential forgetting, 'alpha' may be used as follows:

$$parameter(n) = parameter(n - 1) * (1 - \text{alpha}) + \text{new\_info} * \text{alpha} \quad \text{(Eq. 36)}$$

wherein alpha defines how much of history one wants to remember (how soon to forget). If alpha is 0.01, then in 1/0.01 (i.e., time constant of 100) samples, 63% of previous information is forgotten. Accordingly, if a sampling rate is 12 samples/hr, then 63% of the signal would be forgotten by 100 samples, e.g., ~8 hours. In such example, it would follow that with 3 time parameters or constants, which is about 1 day, only 5% (i.e., 0.37*0.37*0.37=0.05) of signal left from previous day would remain. In the above equation, alpha is a "forgetting factor." Alpha may vary between 0 and 1, and its value dictates how fast old measurements are forgotten by the model. For values of alpha close to 1, the model adapts more quickly to recent measurements. For values of alpha close to 0, the model adapts more slowly to recent measurements. The value of alpha may depend on the elapsed time since the sensor was implanted. The calculation may be recursive or non-recursive.

One example of a noise detection algorithm, as described in more detail in U.S. Pat. No. 8,260,393, which is incorporated herein by reference, is used to quantify the sensor data as clean or noisy (light, medium or severe) based on the amplitude of noise and the difference between raw sensor and filtered sensor signal. The noise duration metric is determined based on the length of noise of a certain severity. For example, the detection of noise episodes of a certain severity (predetermined level of noise) for a certain length of time (for example 2 hours) would increment this metric.

One example of a physiologic noise metrics determined based on algorithms that evaluate the various aspects of the sensor signal related to noise: skewness of a short duration (e.g., 2 hours) of noise, average rate of negative change of signal within this episode, and the number of peaks and valleys in the episode (number of rotations), for example. Once these parameters are calculated, a noise factor (e.g., between 0 and 1) is calculated by combining each parameter as may be appreciated by one skilled in the art. The parameters and/or the physiologic noise factor may be smoothed, for example using an exponential forgetting factor.

Figure 21:
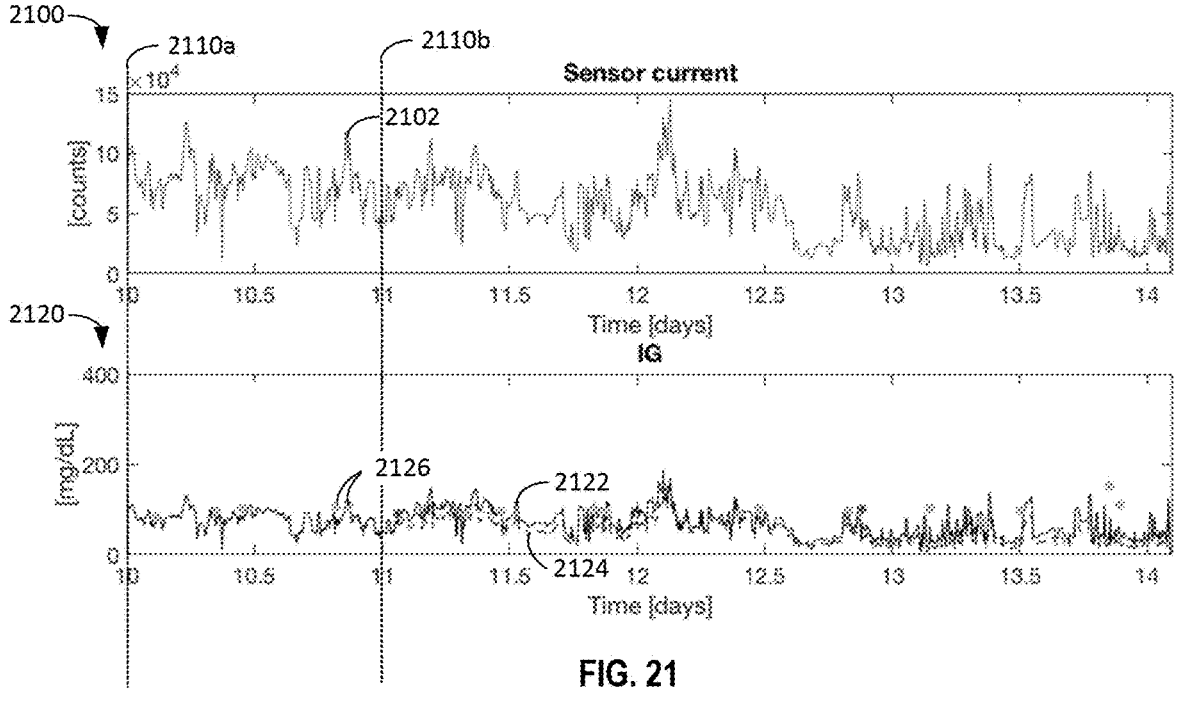
FIG. 21 illustrates another set of relationships between a sensor signal and IG levels estimated via a global calibration model, phase-specific calibration models, and self-measured blood glucose levels, in accordance with some embodiments.

For example, FIG. 21 illustrates a first plot 2100 including a sensor signal 2102 and a second plot 2121 including an IG level 2122 estimated by a global calibration model, an IG level 2124 estimated by $M_s$ before time $T_{switch1}$ 2110a and $M_l$ thereafter, SMBG references 2126 (dots), and a reference $T_{switch2}$ 2110b indicating when a switch would take place utilizing only SMBG references 2126. As shown, utilizing only SMBG references 2126, as previously described in connection with FIG. 20, would result in a selection of the loss model $M_l$ at $T_{switch2}$ 2110b. However, by further utilizing signal-based metrics in the selection of a calibration model, selection of the loss model $M_l$ may be made much earlier, for example, at $T_{switch1}$ 2110a, thereby validating selection based on both SMBG and signal-based metrics within the sensor signal.

Figure 22:
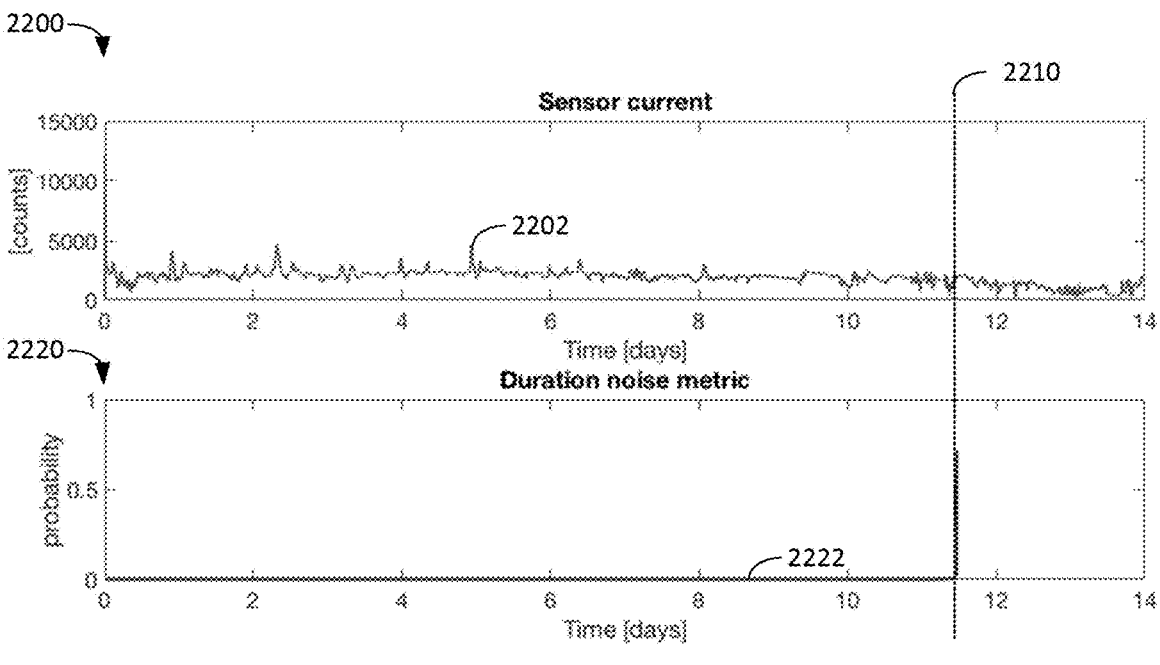
FIG. 22 illustrates a relationship between a sensor signal and a noise metric utilized in selecting a phase-specific calibration model, in accordance with some embodiments.

In some embodiments, selection of a candidate calibration model may be made based on signal-based metrics alone, without the use of SMBGs in the determination. For example, FIG. 22 illustrates a first plot 2200 including a sensor signal 2202 and a second plot 2222 including a trace 2222 indicating a probability that a noise metric is present in sensor signal 2202, and a reference $T_{switch}$ 2210 indicating when a switch would take place based on probability trace 2222 exceeding a threshold (e.g., 0.5). As shown, utilizing only sensor-based metrics present in sensor signal 2202, selection of the loss model $M_l$ at $T_{switch}$ 2210 may be determined, thereby validating selection based on signal-based metrics within the sensor signal alone.

Figure 23:
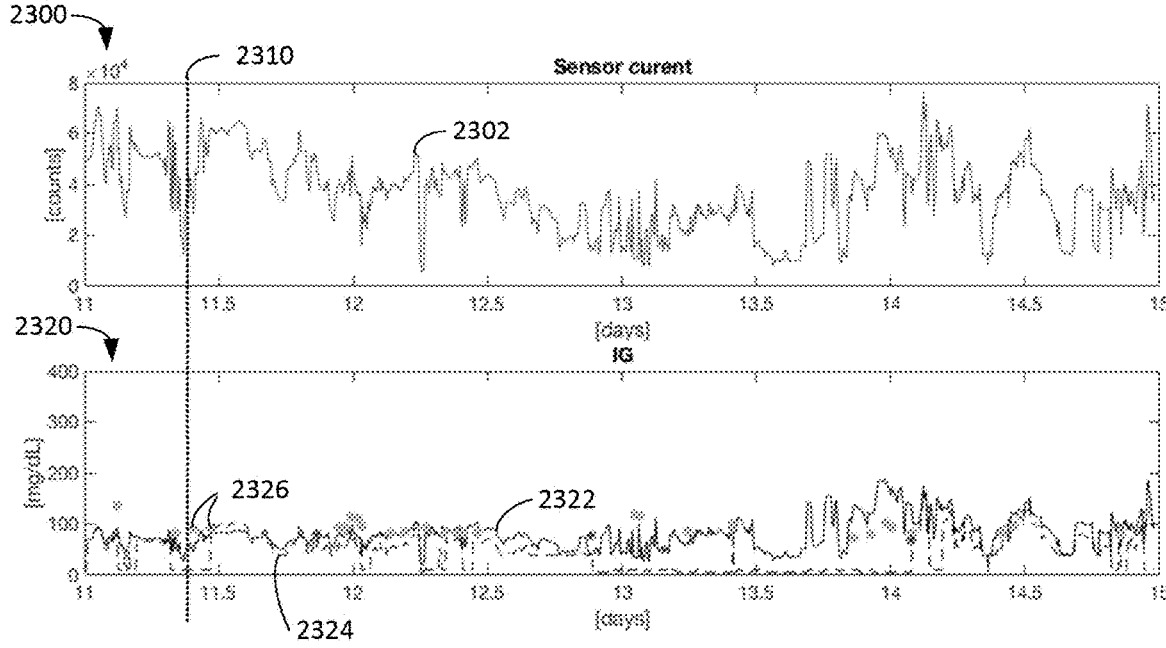
FIG. 23 illustrates a set of relationships between a sensor signal and IG levels estimated via a global calibration model, phase-specific calibration models, and self-measured blood glucose levels, in accordance with some embodiments.

Further to selection of a candidate calibration model based on signal-based metrics alone, FIG. 23 illustrates a first plot 2300 including a sensor signal 2302 and a second plot 2323 including an IG level 2322 estimated by a global calibration model, an IG level 2324 estimated by $M_s$ before time $T_{switch}$ 2310 and $M_l$ thereafter, and SMBG references 2326 (dots). As shown, utilizing only signal-based metrics, for example a noise duration metric as previously described in connection with FIG. 22, would result in a selection of the loss model $M_l$ at $T_{switch}$ 2310. As can be seen, estimated IG level 2322 utilizing the loss model $M_l$ tracks SMBG samples 2326 much more accurately than estimated IG level 2324 utilizing a static global calibration model, after $T_{switch}$ 2310, thereby validating selection based on signal-based metrics within the sensor signal alone.

The Bayesian Calibration approach described herein provides the statistical framework for selecting the best calibration model based on glucose sensor characteristics, auxiliary sensor readings (e.g. impedance, nonenzyme sensors, temperature, or acceleration), and blood glucose calibration as available. Such an approach provides rules that give rise to a more accurate description of outlier behaviors not easily or accurately captured by a static global calibration model approach of the type that is conventionally employed. Where sensor life depends on subject physiology and manufacturing variability, the present application enables selection of a calibration model from several candidate calibration models that describe different cases of the device-physiology interface state, e.g., stable sensitivity versus declining sensitivity. Where day one behavior depends on subject physiology and variations in sensor insertion, the present application enables selection from the candidate calibration models with no dip and recover, moderate, or severe dip-and-recover time profiles across, e.g., day one. The present application further contemplates retrospective fitting of the data provided by and for monitors described herein for health care providers.

Thus, the various embodiments of the methods, processes and systems disclosed herein overcome many of the deficiencies of conventional glucose monitoring systems by providing a system having improved accuracy while also reducing the frequency at which calibrations are required. These objectives are achieved using calibration models that are selected in accordance with rules that specify when each of the various calibration models are most applicable during a monitoring session.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for monitoring a blood glucose level of a user, the method comprising:
   receiving a time-varying electrical signal from an analyte sensor;
   detecting a start of a temporal phase of a monitoring session, the detecting being based at least in part on an evaluation of a noise component of the time-varying electrical signal, wherein the evaluation of the noise component corresponds to the start of the temporal phase of the monitoring session;
   selecting a calibration model from a plurality of candidate calibration models, the selected calibration model comprising one or more calibration model parameters, the selecting of the calibration model being based at least in part on the temporal phase of the monitoring session;
   estimating at least one calibration model parameters of the selected calibration model based on at least the time-varying electrical signal during the temporal phase of the monitoring session;
   estimating the blood glucose level of the user based on the selected calibration model and using the estimated at least one of the one or more calibration model parameters of the selected calibration model; and
   displaying the blood glucose level of the user on a display.

2. The method of claim 1, further comprising receiving a reference input.

3. The method of claim 2, wherein the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

4. The method of claim 1, wherein selecting the calibration model is based at least in part on the selected calibration model having a highest probability, of the plurality of candidate calibration models, of predicting an actual blood glucose level of the user utilizing the time-varying electrical signal.

5. The method of claim 4, wherein the probability is a Bayesian probability.

6. The method of claim 1, wherein selecting the calibration model is based at least in part on detecting a pattern corresponding to the selected calibration model in the time-varying electrical signal.

7. The method of claim 1, wherein estimating at least one of the one or more calibration model parameters of the selected calibration model comprises:

setting the one or more calibration model parameters to an initial value;

transforming the time-varying electrical signal into an estimated interstitial glucose level of the user utilizing the selected calibration model and the initial value of the one or more calibration model parameters;

estimating the blood glucose level based on the estimated interstitial glucose level;

updating the one or more calibration model parameters based on a difference between the estimated blood glucose level and a reference input of the blood glucose level of the user; and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

8. The method of claim 7, wherein the predefined relationship comprises at least one of the estimated interstitial glucose level and the estimated blood glucose level being within a predetermined accuracy of the reference input of the blood glucose level.

9. The method of claim 7, wherein the initial value of the one or more calibration model parameters is a prior average value for the one or more calibration model parameters.

10. The method of claim 1, wherein the plurality of candidate calibration models comprise a common global calibration model, each utilizing one or more unique calibration model parameters.

11. The method of claim 10, wherein the global calibration model comprises a first portion corresponding to a baseline behavior of the analyte sensor and a second portion corresponding to a sensitivity of the analyte sensor.

12. The method of claim 1, wherein the time-varying electrical signal comprises a plurality of sensor data points.

13. An apparatus configured to monitor a blood glucose level of a user, the apparatus comprising:

a memory;

a display; and a processor configured to perform operations comprising:

receiving a time-varying electrical signal from an analyte sensor, detecting a start of a temporal phase of a monitoring session, the detecting being based at least in part on an evaluation of a noise component of the time-varying electrical signal, wherein the evaluation of the noise component corresponds to the start of the temporal phase of the monitoring session, selecting a calibration model from a plurality of candidate calibration models, the selected calibration model comprising one or more calibration model parameters, the selecting of the calibration model being based at least in part on the temporal phase of the monitoring session, estimating at least one of the one or more calibration model parameters of the selected calibration model based on at least the time-varying electrical signal and a reference input during the temporal phase of the monitoring session, estimating the blood glucose level of the user based on the selected calibration model and using the estimated at least one of the one or more calibration model parameters of the selected calibration model, and displaying the blood glucose level of the user on the display.

14. The apparatus of claim 13, further comprising the analyte sensor.

15. The apparatus of claim 13, the operations further comprising receiving the reference input.

16. The apparatus of claim 15, wherein the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

17. The apparatus of claim 13, the selecting of the calibration model being based at least in part on the selected calibration model having a highest probability, of the plurality of candidate calibration models, of predicting an actual blood glucose level of the user utilizing the time-varying electrical signal.

18. The apparatus of claim 17, wherein the probability is a Bayesian probability.

19. The apparatus of claim 13, the selecting of the calibration model being based at least in part on detecting a pattern corresponding to the selected calibration model in the time-varying electrical signal.

20. The apparatus of claim 13, the operations further comprising estimating at least one of the one or more calibration model parameters of the selected calibration model by:

setting the one or more calibration model parameters to an initial value;

transforming the time-varying electrical signal into an estimated interstitial glucose level of the user utilizing the selected calibration model and the initial value of the one or more calibration model parameters;

estimating the blood glucose level based on the estimated interstitial glucose level;

updating the one or more calibration model parameters based on a difference between the estimated blood glucose level and the reference input of the blood glucose level of the user; and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

21. The apparatus of claim 20, wherein the predefined relationship comprises at least one of the estimated interstitial glucose level and the estimated blood glucose level being within a predetermined accuracy of the reference input of the blood glucose level.

22. The apparatus of claim 20, wherein the initial value of the one or more calibration model parameters is a prior average value for the one or more calibration model parameters.

23. The apparatus of claim 13, wherein the plurality of candidate calibration models comprise a common global calibration model, each utilizing one or more unique calibration model parameters.

24. The apparatus of claim 23, wherein the global calibration model comprises a first portion corresponding to a baseline behavior of the analyte sensor and a second portion corresponding to a sensitivity of the analyte sensor.

25. The apparatus of claim 13, wherein the time-varying electrical signal comprises a plurality of sensor data points.

26. A non-transitory, computer-readable medium comprising code that, when executed, causes a processor of an apparatus configured to monitor a blood glucose level of a user to perform operations comprising:

receiving a time-varying electrical signal from an analyte sensor;

detecting a start of a temporal phase of a monitoring session, the detecting being based at least in part on an evaluation of a noise component of the time-varying electrical signal, wherein the evaluation of the noise component corresponds to the start of the temporal phase of the monitoring session;

selecting a calibration model from a plurality of candidate calibration models, the selected calibration model comprising one or more calibration model parameters, the selecting of the calibration model being based at least in part on the temporal phase of the monitoring session;

estimating at least one of the one or more calibration model parameters of the selected calibration model based on at least the time-varying electrical signal and a reference input during the temporal phase of the monitoring session;

estimating the blood glucose level of the user based on the selected calibration model and using the estimated at least one of the one or more calibration model parameters of the selected calibration model; and displaying the blood glucose level of the user on a display.

27. The non-transitory, computer-readable medium of claim 26, further comprising code that, when executed, the operations further comprising receiving the reference input.

28. The non-transitory, computer-readable medium of claim 27, wherein the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

29. The non-transitory, computer-readable medium of claim 26, wherein selecting the calibration model is based at least in part on the selected calibration model having a highest probability, of the plurality of candidate calibration models, of predicting an actual blood glucose level of the user utilizing the time-varying electrical signal.

30. The non-transitory, computer-readable medium of claim 29, wherein the probability is a Bayesian probability.

31. The non-transitory, computer-readable medium of claim 26, wherein selecting the calibration model is further based at least in part on detecting a pattern corresponding to the selected calibration model in the time-varying electrical signal.

32. The non-transitory, computer-readable medium of claim 26, wherein estimating at least one of the one or more calibration model parameters of the selected calibration model comprises:

setting the one or more calibration model parameters to an initial value;

transforming the time-varying electrical signal into an estimated interstitial glucose level of the user utilizing the selected calibration model and the initial value of the one or more calibration model parameters;

estimating the blood glucose level based on the estimated interstitial glucose level;

updating the one or more calibration model parameters based on a difference between the estimated blood glucose level and the reference input of the blood glucose level of the user; and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

33. The non-transitory, computer-readable medium of claim 32, wherein the predefined relationship comprises at least one of the estimated interstitial glucose level and the estimated blood glucose level being within a predetermined accuracy of the reference input of the blood glucose level.

34. The non-transitory, computer-readable medium of claim 32, wherein the initial value of the one or more calibration model parameters is a prior average value for the one or more calibration model parameters.

35. The non-transitory, computer-readable medium of claim 32, wherein the plurality of candidate calibration models comprise a common global calibration model, each utilizing one or more unique calibration model parameters.

36. The non-transitory, computer-readable medium of claim 35, wherein the global calibration model comprises a first portion corresponding to a baseline behavior of the analyte sensor and a second portion corresponding to a sensitivity of the analyte sensor.

37. The non-transitory, computer-readable medium of claim 32, wherein the time-varying electrical signal comprises a plurality of sensor data points.

38. A method for monitoring a blood glucose level of a user, the method comprising:

receiving time-varying electrical signals from an analyte sensor during at least first and second temporal phases of a monitoring session, each of the first and second temporal phases being different phases of the monitoring session;

selecting a first calibration model from a plurality of candidate calibration models for the first temporal phase, the first calibration model comprising one or more calibration model parameters;

selecting a second calibration model for the second temporal phase, the second calibration model comprising one or more calibration model parameters, and the second calibration model being different than the first calibration model;

estimating at least one of the one or more calibration model parameters of the first calibration model based at least in part on a portion of the time-varying electrical signals received during the first temporal phase;

estimating at least one of the one or more calibration model parameters of the second calibration model based at least in part on a portion of the time-varying electrical signals received during the second temporal phase;

estimating the blood glucose level of the user during the first temporal phase based at least in part on the first calibration model using the at least one estimated parameter of the first calibration model;

estimating the blood glucose level of the user during the second temporal phase based at least in part on the second calibration model using the at least one estimated parameter of the second calibration model;

determining at least one of a start or an end of the first temporal phase or the second temporal phase based on an evaluation of a noise component of the time-varying electrical signal satisfying a threshold; and displaying the blood glucose level of the user during the first temporal phase or the blood glucose level of the user during the second temporal phase on a display.

39. The method of claim 38, further comprising receiving a reference input.

40. The method of claim 39, wherein the reference input comprises at least one of a blood glucose reference, a noise metric of the time-varying electrical signal, an impedance of the analyte sensor, an input from a sensor configured to measure at least one of an acceleration of the user, a temperature and an atmospheric pressure.

41. The method of claim 38, wherein selecting the first and second calibration models is based at least in part on the selected first and second calibration models having a highest probability, of the plurality of candidate calibration models, of predicting during the first and second temporal phases, respectively, an actual blood glucose level of the user utilizing the time-varying electrical signals.

42. The method of claim 41, wherein the probability is a Bayesian probability.

43. The method of claim 38, wherein selecting at least one of the first and second calibration models is further based at least in part on detecting a pattern corresponding to the selected calibration model in the time-varying electrical signal.

44. The method of claim 38, wherein estimating at least one of the one or more calibration model parameters of the selected first or second calibration model comprises:

setting the one or more calibration model parameters to an initial value;

transforming the time-varying electrical signal into an estimated interstitial glucose level of the user utilizing the selected calibration model and the initial value of the one or more calibration model parameters;

estimating the blood glucose level based on the estimated interstitial glucose level;

updating the one or more calibration model parameters based on a difference between the estimated blood glucose level and a reference input of the blood glucose level of the user; and recursively re-estimating the interstitial glucose level and the blood glucose level based on the selected calibration model and the one or more updated calibration model parameters until a predefined relationship between the reference input of the blood glucose level of the user and at least one of the estimated interstitial glucose level and the estimated blood glucose level is present.

45. The method of claim 44, wherein the predefined relationship comprises at least one of the estimated interstitial glucose level and the estimated blood glucose level being within a predetermined accuracy of the reference input of the blood glucose level.

46. The method of claim 44, wherein the initial value of the one or more calibration model parameters is a prior average value for the one or more calibration model parameters.

47. The method of claim 38, wherein the time-varying electrical signals each comprises a plurality of sensor data points.

48. An apparatus configured to monitor a blood glucose level of a user, the apparatus comprising:

a memory;

a display; and a processor configured to perform operations comprising:

receiving time-varying electrical signals from an analyte sensor during at least first and second temporal phases of a monitoring session, each of the first and second temporal phases being different phases of the monitoring session, selecting a first calibration model from a plurality of calibration models for the first temporal phase, the first calibration model comprising one or more calibration model parameters, selecting a second calibration model for the second temporal phase, the second calibration model comprising one or more calibration model parameters, and the second calibration model being different than the first calibration model, estimating at least one of the one or more calibration model parameters of the first calibration model based at least in part on a portion of the time-varying electrical signals received during the first temporal phase, estimating at least one of the one or more calibration model parameters of the second calibration model based at least in part on the time-varying electrical signals received during the second temporal phase, estimating the blood glucose level of the user during the first temporal phase based at least in part on the first calibration model using the at least one estimated parameter of the first calibration model, estimating the blood glucose level of the user during the second temporal phase based at least in part on the second calibration model using the at least one estimated parameter of the second calibration model, determining at least one of a start or an end of the first temporal phase or the second temporal phase based on an evaluation of a noise component of the time-varying electrical signal satisfying a threshold, and displaying the blood glucose level of the user during the first temporal phase or the blood glucose level of the user during the second temporal phase on the display.

* * * * *